(12) United States Patent
Saidi et al.

(10) Patent No.: US 7,933,848 B2
(45) Date of Patent: *Apr. 26, 2011

(54) SUPPORT VECTOR REGRESSION FOR CENSORED DATA

(75) Inventors: Olivier Saidi, Greenwich, CT (US); David A. Verbel, New York, NY (US)

(73) Assignee: Aureon Laboratories, Inc., Yonkers, NY (US)

( * ) Notice: Subject to any disclaimer, the term of this patent is extended or adjusted under 35 U.S.C. 154(b) by 168 days.

This patent is subject to a terminal disclaimer.

(21) Appl. No.: 12/322,329

(22) Filed: Jan. 30, 2009

(65) Prior Publication Data

US 2010/0005042 A1    Jan. 7, 2010

Related U.S. Application Data

(63) Continuation of application No. 10/991,240, filed on Nov. 17, 2004, now Pat. No. 7,505,948.

(60) Provisional application No. 60/520,939, filed on Nov. 18, 2003.

(51) Int. Cl.
*G06E 1/00* (2006.01)
*G06E 3/00* (2006.01)
*G06G 7/00* (2006.01)

(52) U.S. Cl. ........................................ 706/14

(58) Field of Classification Search .................... 706/14
See application file for complete search history.

(56) References Cited

U.S. PATENT DOCUMENTS

| 5,953,707 A * | 9/1999 | Huang et al. ............... 705/10 |
| 6,195,624 B1 * | 2/2001 | Woodman et al. ............ 703/7 |
| 2004/0128112 A1 * | 7/2004 | Mikytuck et al. .......... 702/190 |

OTHER PUBLICATIONS

Annette M. Molinaro, Sandrine Dudoit, and Mark J. van der Laan, "Tree-based Multivariate Regression and Density Estimation with Right-Censored Data" (Sep. 2003). U.C. Berkeley Division of Biostatistics Working Paper Series. Working Paper 135.*
Alex J. Smola, Bernhard Scholkopf. "A Tutorial on Support Vector Regression" NeuroColt2 Technical Report Series Oct. 1998.*
Alain Rakotomamonjy "Variable Selection Using SVM based Criteria" Journal of Machine Learning Research Mar. 2003.*

* cited by examiner

*Primary Examiner* — Jeffrey A Gaffin
*Assistant Examiner* — Ben M Rifkin
(74) *Attorney, Agent, or Firm* — Mintz, Levin, Cohn, Ferris, Glovsky & Popeo, P.C.

(57) ABSTRACT

A method of producing a model for use in predicting time to an event includes obtaining multi-dimensional, non-linear vectors of information indicative of status of multiple test subjects, at least one of the vectors being right-censored, lacking an indication of a time of occurrence of the event with respect to the corresponding test subject, and performing regression using the vectors of information to produce a kernel-based model to provide an output value related to a prediction of time to the event based upon at least some of the information contained in the vectors of information, where for each vector comprising right-censored data, a censored-data penalty function is used to affect the regression, the censored-data penalty function being different than a non-censored-data penalty function used for each vector comprising non-censored data.

41 Claims, 5 Drawing Sheets

SUPPORT VECTOR REGRESSION FOR CENSORED DATA

CROSS-REFERENCE TO RELATED APPLICATION

This application is a continuation of U.S. patent application Ser. No. 10/991,240, filed Nov. 17, 2004 (now U.S. Pat. No. 7,505,948), which claims the benefit of U.S. Provisional Application No. 60/520,939 filed Nov. 18, 2003, the entire disclosures of which are hereby incorporated by reference herein in their entireties.

FIELD OF THE INVENTION

The invention relates to time-to-event analyses and in particular time-to-event analyses of right-censored data.

BACKGROUND OF THE INVENTION

There are many instances in which it is desirable to predict the likelihood of an event occurring (initially occurring and/or recurring) within a certain amount of time and/or the amount of time until an event is likely to occur. In the medical field, for example, it would be useful to predict whether a patient who has been treated for a particular disease is likely to recur, and if so, when. Mathematical models can be developed to make such time-to-event predictions based on data obtained from actual cases. In the example above, such a predictive model could be developed by studying a cohort of patients who were treated for a particular disease and identifying common characteristics or "features" that distinguished patients who recur from those who do not. By taking into account the actual time to recurrence for the patients in the cohort, features and values of features can also be identified that correlate to patients that recurred at particular times. These features can be used to predict the time to recurrence for a future patient based on that patient's individual feature profile. Such time-to-event predictions can help a treating physician assess and plan the treatment for the occurrence of the event.

A unique characteristic of time-to-event data is that the event of interest (in this example disease recurrence) may not yet be observed. This would occur, for example, where a patient in the cohort visits the doctor but the disease has not yet recurred. Data corresponding to such a patient visit is referred to as "right-censored" because as of that time some of the data of interest is missing (i.e., the event of interest, e.g., disease recurrence, has not yet occurred). Although censored data by definition lacks certain information, it can be very useful, if the censored nature can be accounted for, in developing predictive models because it provides more data points for use in adapting parameters of the models. Indeed, time-to-event data, especially right-censored time-to-event data, is one of the most common types of data used in clinical, pharmaceutical, and biomedical research.

In forming or training predictive mathematical models, it is generally desirable to incorporate as much data as possible from as many sources as possible. Thus, for example, for health time-to-event predictions, for example, it is generally desirable to have data from as many patients as possible and as much relevant data from each patient as possible. With these large amounts of diverse data, however, come difficulties in how to process all of the information available. Although various models exist, none is completely satisfactory for handling high dimensional, heterogeneous data sets that include right-censored data. For example, the Cox proportional hazards model is a well-known model used in the analysis of censored data for identifying differences in outcome due to patient features by assuming, through its construct, that the failure rate of any two patients are proportional and the independent features of the patients affect the hazard in a multiplicative way. But while the Cox model can properly process right-censored data, the Cox model is not ideal for analyzing high dimensional datasets since it is limited by the total regression degrees of freedom in the model as well as it needing a sufficient number of patients if dealing with a complex model. Support Vector Machines (SVMs) on the other hand, perform well with high dimensional datasets, but are not well-suited for use with censored data.

SUMMARY OF THE INVENTION

In general, in an aspect, the invention provides a method of producing a model for use in predicting time to an event, the method comprising obtaining multi-dimensional, non-linear vectors of information indicative of status of multiple test subjects, at least one of the vectors being right-censored, lacking an indication of a time of occurrence of the event with respect to the corresponding test subject, and performing regression using the vectors of information to produce a kernel-based model to provide an output value related to a prediction of time to the event based upon at least some of the information contained in the vectors of information, where for each vector comprising right-censored data, a censored-data penalty function is used to affect the regression, the censored-data penalty function being different than a non-censored-data penalty function used for each vector comprising non-censored data.

Implementations of the invention may include one or more of the following features. The regression comprises support vector machine regression. The censored-data penalty function has a larger positive slack variable than the non-censored data penalty function does. Performing the regression includes using penalty functions that include linear functions of a difference between a predicted value of the model and a target value for the predicted value, and a first slope of the linear function for positive differences between the predicted and target values for the censored-data penalty function is lower than a second slope of the linear function for positive differences between the predicted and target values for the non-censored-data penalty function. The first slope is substantially equal to a third slope of the linear function for negative differences between the predicted and target values for the censored-data penalty function and a fourth slope of the linear function for negative differences between the predicted and target values for the non-censored-data penalty function, and positive and negative slack variables of the non-censored-data penalty function and a negative slack variable of the censored-data penalty function are substantially equal.

Implementations of the invention may also include one or more of the following features. The data of the vectors are associated with categories based on at least one characteristic of the data that relate to the data's ability to help the model provide the output value such that the output value helps predict time to the event, the method further comprising performing the regression using the data from the vectors in sequence from the category with data most likely, to the category with data least likely, to help the model provide the output value such that the output value helps predict time to the event. The at least one characteristic is at least one of reliability and predictive power. The regression is performed in a greedy-forward manner in accordance with the features of the data to select features to be used in the model. The method further comprises performing a greedy backward procedure to the features of the vectors, after performing the regression, to further select features to be used in the model. The regression is performed in the greedy-forward manner with respect to only a portion of the features of the vectors. The vectors include categories of data of clinical/histopathological data, biomarker data, and bio-image data, and wherein the regression is performed in the greedy-forward manner with respect to only the biomarker data and the bio-image data of the vectors. The vectors of information are indicative of status of test subjects that are at least one of living, previously-living, and inanimate.

In general, in another aspect, the invention provides a computer program product producing a model for use in predicting time to an event, the computer program product residing on a computer readable medium, the computer program product comprising computer-readable, computer-executable instructions for causing a computer to: obtain multi-dimensional, non-linear vectors of information indicative of status of multiple test subjects, at least one of the vectors being right-censored, lacking an indication of a time of occurrence of the event with respect to the corresponding test subject; and perform regression using the vectors of information to produce a kernel-based model to provide an output value related to a prediction of time to the event based upon at least some of the information contained in the vectors of information, where for each vector comprising right-censored data, a censored-data penalty function is used to affect the regression, the censored-data penalty function being different than a non-censored-data penalty function used for each vector comprising non-censored data.

Implementations of the invention may include one or more of the following features. The regression comprises support vector machine regression. The censored-data penalty function has a larger positive slack variable than the non-censored data penalty function does. The instructions for causing the computer to perform the regression include instruction for causing the computer to use penalty functions that include linear functions of a difference between a predicted value of the model and a target value for the predicted value, and a first slope of the linear function for positive differences between the predicted and target values for the censored-data penalty function is lower than a second slope of the linear function for positive differences between the predicted and target values for the non-censored-data penalty function. The first slope is substantially equal to a third slope of the linear function for negative differences between the predicted and target values for the censored-data penalty function and a fourth slope of the linear function for negative differences between the predicted and target values for the non-censored-data penalty function, and positive and negative slack variables of the non-censored-data penalty function and a negative slack variable of the censored-data penalty function are substantially equal.

Implementations of the invention may also include one or more of the following features. The instructions for causing the computer to perform regression cause the regression to be performed using the data from the vectors in sequence from a category with data most likely, to a category with data least likely, to help the model provide the output value such that the output value helps predict time to the event. The instructions for causing the computer to perform regression cause the regression to be performed in a greedy-forward manner in accordance with features of the data to select features to be used in the model. The computer program product further comprises instructions for causing the computer to perform a greedy backward procedure to the features of the model, after performing the regression, to further select features to be used in the model. The instructions for causing the computer to perform regression in the greedy-forward manner cause the computer to perform the greedy-forward feature selection with respect to only a portion of the features of the vectors. The vectors include categories of data of clinical/histopathological data, biomarker data, and bio-image data, and wherein the instructions for causing the computer to perform regression in the greedy-forward manner cause the computer to perform the greedy-forward feature selection with respect to only the biomarker data and the bio-image data of the vectors.

In general, in another aspect, the invention provides a method of producing a model for use in predicting time to an event, the method comprising obtaining multi-dimensional, non-linear vectors of information indicative of status of multiple test subjects, and performing regression using the vectors of information to produce a kernel-based model to provide an output value related to a prediction of time to the event based upon at least some of the information contained in the vectors of information, where the data of the vectors are associated with categories based on at least one characteristic of the data that relate to the data's ability to help the model provide the output value such that the output value helps predict time to the event, and where the regression is performed using the data from the vectors in sequence from the category with data most likely, to the category with data least likely, to help the model provide the output value such that the output value helps predict time to the event.

Implementations of the invention may include one or more of the following features. The regression is performed in a greedy-forward manner in accordance with features of the data to select features to be used in the model. The method further comprises performing a greedy backward procedure to the features of the vectors, after performing the regression, to further select features to be used in the model. The regression is performed in the greedy-forward manner with respect to only a portion of the features of the vectors. The vectors include categories of data of clinical/histopathological data, biomarker data, and bio-image data, and wherein the regression is performed in a non-greedy-forward manner with the clinical/histopathological data and in the greedy-forward manner with respect to only the biomarker data and the bio-image data of the vectors, in that order. At least one of the vectors is right-censored, lacking an indication of a time of occurrence of the event with respect to the corresponding test subject.

In general, in another aspect, the invention provides a computer program product for producing a model for use in predicting time to an event, the computer program product residing on a computer readable medium and comprising computer-readable, computer-executable instructions for causing a computer to: obtain multi-dimensional, non-linear vectors of information indicative of status of multiple test subjects, at least one of the vectors being right-censored, lacking an indication of a time of occurrence of the event with respect to the corresponding test subject; and perform regression using the vectors of information to produce a kernel-based model to provide an output value related to a prediction of time to the event based upon at least some of the information contained in the vectors of information, where the data of the vectors are associated with categories based on at least one characteristic of the data that relate to the data's ability to help the model provide the output value such that the output value helps predict time to the event, and where the regression is performed using the data from the vectors in sequence from the category with data most likely, to the category with data least likely, to help the model provide the output value such that the output value helps predict time to the event.

Implementations of the invention may include one or more of the following features. The regression is performed in a greedy-forward manner in accordance with features of the data to select features to be used in the model. The computer program product further comprises instructions for causing the computer to perform a greedy backward procedure to the features of the vectors, after performing the regression, to further select features to be used in the model. The regression is performed in the greedy-forward manner with respect to only a portion of the features of the vectors. The vectors include categories of data of clinical/histopathological data, biomarker data, and bio-image data, and wherein the regression is performed in a non-greedy-forward manner with the clinical/histopathological data and in the greedy-forward manner with respect to only the biomarker data and the bio-image data of the vectors, in that order.

In general, in another aspect, the invention provides a method of determining a predictive diagnosis for a patient, the method comprising receiving at least one of clinical and histopathological data associated with the patient, receiving biomarker data associated with the patient, receiving bio-image data associated with the patient, and applying at least a portion of the at least one of clinical and histopathological data, at least a portion of the biomarker data, and at least a portion of the bio-image data to a kernel-based mathematical model to calculate a value indicative of a diagnosis for the patient.

Implementations of the invention may include one or more of the following features. The at least a portion of the biomarker data comprises data for less than all biomarker features of the patient. The at least a portion of the biomarker data comprises data for less than about ten percent of all biomarker features of the patient. The at least a portion of the biomarker data comprises data for less than about five percent of all biomarker features of the patient. The at least a portion of the biomarker data comprises data for less than all bio-image features of the patient. The at least a portion of the biomarker data comprises data for less than about one percent of all bio-image features of the patient. The at least a portion of the biomarker data comprises data for less than about 0.2 percent of all bio-image features of the patient. The value is indicative of at least one of a time to recurrence of a health-related condition and a probability of recurrence of the health-related condition.

In general, in another aspect, the invention provides an apparatus for determining time-to-event predictive information, the apparatus comprising an input configured to obtain multi-dimensional, non-linear first data associated with a possible future event, and a processing device configured to use the first data in a kernel-based mathematical model, derived at least partially from a regression analysis of multi-dimensional, non-linear, right-censored second data that determines parameters of the model that affect calculations of the model, to calculate the predictive information indicative of at least one of a predicted time to the possible future event and a probability of the possible future event.

Implementations of the invention may include one or more of the following features. The input and the processing device comprise portions of a computer program product residing on a computer readable medium, the computer program product comprising computer-readable, computer-executable instructions for causing a computer to obtain the first data and to use the first data in the mathematical model to calculate the predictive information. The first data comprises at least one of clinical and histopathological data, biomarker data, and bio-image data associated with a patient, and wherein the processing device is configured to use at least a portion of the at least one of clinical and histopathological data, at least a portion of the biomarker data, and at least a portion of the bio-image data to a kernel-based mathematical model to calculate the predictive information for the patient. The at least a portion of the biomarker data comprises data for less than all biomarker features of the patient. The at least a portion of the biomarker data comprises data for less than about five percent of all biomarker features of the patient. The at least a portion of the biomarker data comprises data for less than all bio-image features of the patient. The at least a portion of the biomarker data comprises data for less than about 0.2 percent of all bio-image features of the patient.

In general, in another aspect, the invention provides a computer program product for determining a predictive diagnosis for a patient, the computer program product residing on a computer readable medium and comprising computer-readable, computer-executable instructions for causing a computer to: receive at least one of clinical and histopathological data associated with the patient; receive biomarker data associated with the patient; receive bio-image data associated with the patient; and apply at least a portion of the at least one of clinical and histopathological data, at least a portion of the biomarker data, and at least a portion of the bio-image data to a kernel-based mathematical model to calculate a value indicative of a diagnosis for the patient.

Implementations of the invention may include one or more of the following features. The at least a portion of the biomarker data comprises data for less than all biomarker features of the patient. The computer program product of claim 50 wherein the at least a portion of the biomarker data comprises data for less than about ten percent of all biomarker features of the patient. The at least a portion of the biomarker data comprises data for less than about five percent of all biomarker features of the patient.

Implementations of the invention may also include one or more of the following features. The at least a portion of the biomarker data comprises data for less than all bio-image features of the patient. The at least a portion of the biomarker data comprises data for less than about one percent of all bio-image features of the patient. The at least a portion of the biomarker data comprises data for less than about 0.2 percent of all bio-image features of the patient. The value is indicative of at least one of a time to recurrence of a health-related condition and a probability of recurrence of the health-related condition.

The invention provides novel techniques, e.g., to take advantage of the high-dimensional capability of SVR while adapting it for use with censored data, in particular right-censored data. Support vector regression for censored data (SVRc) may provide numerous benefits and capabilities. Because much of the information available to form or train a predictive model may be censored, SVRc can increase model predictive accuracy by using censored data as well as uncensored data in SVR analyses. With SVRc, high-dimensional data with few outcome data points, including right-censored observations, may be used to produce a time-to-event predictive model. Features of high-dimensional data may be pared down to leave a reduced set of features used in a model for time-to-event prediction such that time-to-event prediction accuracy can be improved.

These and other capabilities of the invention, along with the invention itself, will be more fully understood after a review of the following figures, detailed description, and claims.

DETAILED DESCRIPTION OF PREFERRED EMBODIMENTS

Figure 1:
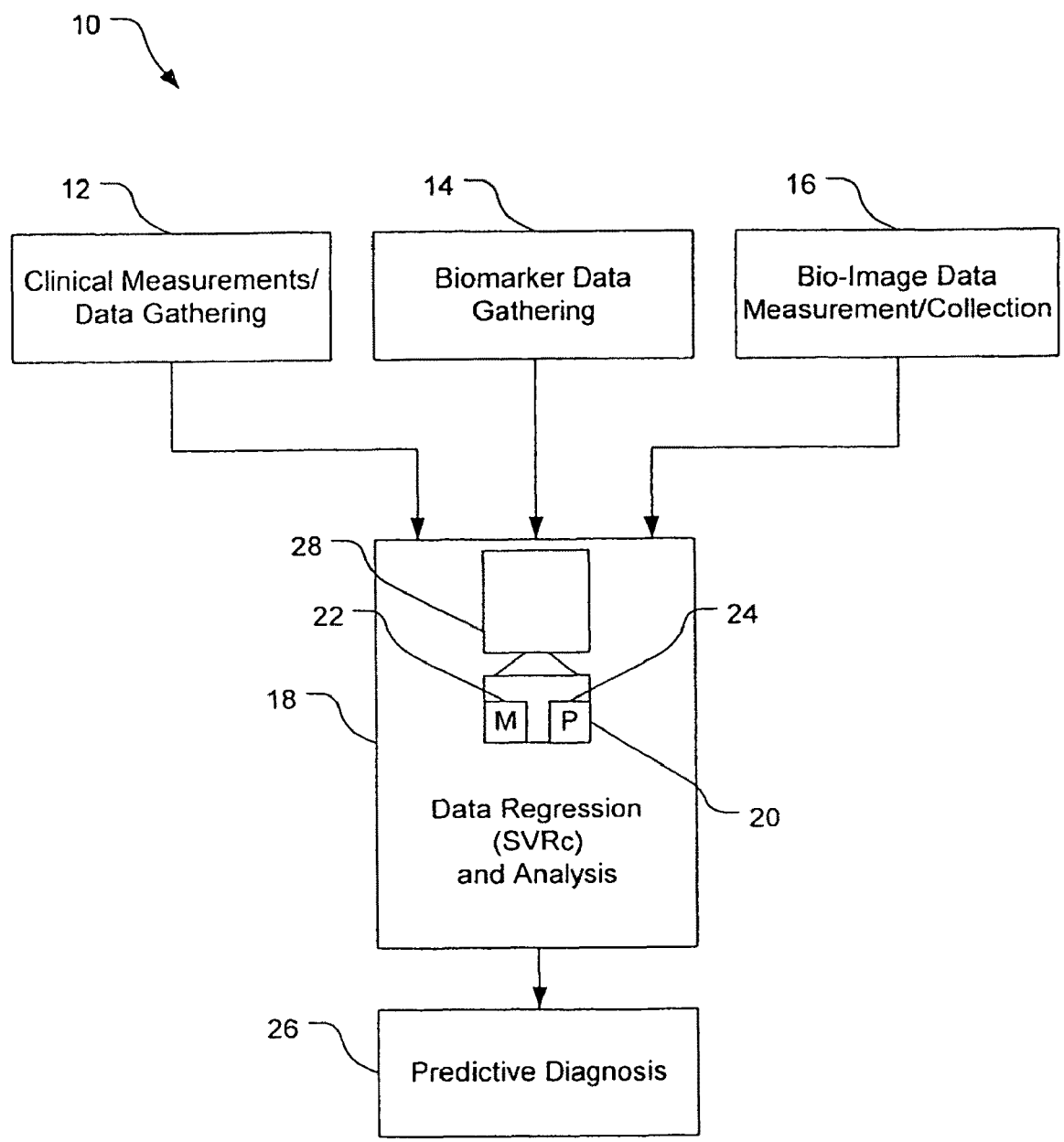
FIG. 1 is a simplified block diagram of a predictive diagnostic system for use with right-censored data.

Embodiments of the invention provide techniques for improving accuracy of predicting time-to-event probability. To develop an improved model for predicting time-to-event probability, a novel modified loss/penalty function is used within a Support Vector Machine (SVM) for right-censored, heterogeneous data. Using this new modified loss/penalty function, the SVM can meaningfully process right-censored data to thereby perform Support Vector Regression on censored data (referred to here as SVRc). Data for developing the model may be from a variety of test subjects, the subjects depending upon the desired event to be predicted. For example, test subjects could be living or previously-living subjects such as humans or other animals for medical applications. Test subjects may also, or alternatively, be inanimate objects for medical or non-medical applications. For example, inanimate test subjects could be car parts for wear analysis, financial reports such as stock performance for financial services, etc.

In exemplary embodiments, SVRc can be used to produce a model for predicting recurrence of cancer. Such a model might analyze features from three different feature domains taken from a patient cohort population: (i) clinical/histopathological features, (ii) biomarker features, and (iii) bio-imaging features, where features are added to the model in phases, with features selected from different domains serving as anchors for the subsequent phases.

Clinical features refer to patient-specific data that can be collected by the physician during a routine office visit. These data can include demographic information such as age, race, gender, etc. and some disease-related information, such as clinical staging or lab parameters, such as prostate-specific antigen (PSA).

Histopathological features refer to information pertaining to pathology that describes the essential nature of the disease, especially the structural and functional changes in tissues and organs of the body caused by the disease. Examples of histopathological features include the Gleason grade and score, surgical margin status, and ploidy information.

Biomarker features refer to information relating to biochemicals in the body having particular molecular features that make them useful for measuring the progress of a disease or the effects of treatment. An example of a type of biomarker feature is information pertaining to the use of an antibody to identify a specific cell type, cell organelle, or cell component. Biomarker features could include, for example, the percent of the cells in a sample staining positive for several biomarkers and intensity of the stain of these biomarkers.

Bio-imaging features refer to information derived from the use of mathematical and computational sciences to study a digital image from tissue or cells. Examples of such information are the mean, maximum, minimum, and standard deviation of lumen. Examples of clinical/histopathological features, biomarker features, and bio-imaging features appear in the Appendix. These various features can be obtained and analyzed through the use of commercially available software such as Cellenger from Definiens AG (www.definiens.com) and MATLAB from The MathWorks, Inc. (www.mathworks.com).

In this example, the features from these three domains are added to the model in three phases (e.g. first phase: clinical/histopathological data; second phase: selected clinical/histopathological features are used as an anchor and bio-marker features added; third phase: selected clinical/histopathological and selected biomarker features are used as an anchor and bio-image (IMG) features are added). The resulting model includes the selected features and model parameters iteratively adjusted/tuned to those features. Other embodiments are within the scope of the invention.

Embodiments of the invention may be used in a wide variety of applications. In the medical field, for example, embodiments may be used for predicting time to events such as recurrence of prostate-specific antigen (PSA). Embodiments may also be used for predictive diagnostics for a vast array of ailments or other health-related issues including response to a pharmaceutical drug or hormone, or a radiation or chemotherapy regimen. Further applications include use in tissue-based clinical trials and clinical trials generally. Other applications where the interest is in predicting an event occurring are possible as well. From the health field, examples include predicting infection of kidney dialysis patients, infection for burn patients, and weaning of breast-fed newborns. In other fields, e.g., engineers may be interested in predicting when a brake pad will fail. In a medical-field embodiment shown in FIG. 1, a SVRc system 10 includes data sources of clinical/histopathological measurement/data gathering 12, biomarker data gathering 14, and bio-image data measurement/collection, as well as a data regression and analysis device 18 that provides a predictive diagnosis output 26. The data sources 12, 14, 16 could include appropriate personnel (e.g., doctors), data records (e.g., medical databases), and/or machinery (e.g., imaging devices, staining equipment, etc.). The regression and analysis device 18 includes a computer 20 including memory 22 and a processor 24 configured to execute computer-readable, computer-executable software code instructions for performing SVRc. The computer 20 is shown representatively as a personal computer although other forms of computing devices are acceptable. The device 18 is further configured to provide as the output 26 data that indicate, or can be processed to indicate, a predicted time to an event. For example, the output 26 may be a predictive diagnosis of a time to occurrence (including recurrence) of cancer in a patient. The output 26 may be provided on a display screen 28 of the regression and analysis device 18.

The computer 20 of the regression and analysis device 18 is configured to perform SVRc by providing an SVM that is modified to analyze both censored and non-censored data. The computer 20 can process data according to the following construct of SVRc.

SVRc Construct

A data set T has N samples, $T=\{z_i\}_{i=1}^{N}$ where $z_i=\{x_i, y_i, s_i\}$, where $x_1 \in R^n$ (with R being the set of real numbers) is the sample vector, and $y_i \in R$ is the target value (i.e., the time to occurrence that it is desired to predict), and $s_i \in \{0,1\}$ is the censorship status of the corresponding sample. The sample vector is the vector of features for the i-th (out of N) sample/patient. The target value y is the actual time to the detected event (e.g., recurrence) for non-censored data and the last known time of observation for censored data. If the censorship status $s_i$ is 1, then the $i^{th}$ sample $z_i$ is a censored sample while if $s_i$ is 0, then the $i^{th}$ sample $z_i$ is a non-censored sample. When $s_i$=0 for i=1 . . . N, the data set T becomes a normal, completely uncensored data set. Additionally, datasets where the censorship status $s_i$=1 indicates a non-censored sample and $s_i$=0 indicates a censored sample are also valid; In this case, the SVRc is controlled to consider censorship in the opposite fashion.

The SVRc formulation constructs a linear regression function $$f(x) = W^T \Phi(x) + b \quad (1)$$

on a feature space F with f(x) being the predicted time to event for sample x. Here, W is a vector in F, and $\Phi(x)$ maps the input x to a vector in F. The W and b in (1) are obtained by solving an optimization problem, the general form of which is:

$$\min_{W,b} \frac{1}{2} W^T W$$

$$\text{s.t. } y_i - (W^T \phi(x_i) + b) \le \varepsilon$$

$$(W^T \phi(x_i) + b) - y_i \le \varepsilon$$

This equation, however, assumes the convex optimization problem is always feasible, which may not be the case. Furthermore, it is desired to allow for small errors in the regression estimation. For these reasons, a loss function is used for SVR. The loss allows some leeway for the regression estimation. Ideally, the model built will exactly compute all results accurately, which is infeasible. The loss function allows for a range of error from the ideal, with this range being controlled by slack variables $\xi$ and $\xi^*$, and a penalty C. Errors that deviate from the ideal, but are within the range defined by $\xi$ and $\xi^*$, are counted, but their contribution is mitigated by C. The more erroneous the instance, the greater the penalty. The less erroneous (closer to the ideal) the instance is, the less the penalty. This concept of increasing penalty with error results in a slope, and C controls this slope. While various loss functions may be used, for an epsilon-insensitive loss function, the general equation transforms into:

$$\min_{W,b} P = \frac{1}{2} W^T W + C \sum_{i=1}^{l} (\xi_i + \xi_i^*)$$

$$\text{s.t. } y_i - (W^T \Phi(x_i) + b) \le \varepsilon + \xi_i$$

$$(W^T \Phi(x_i) + b) - y_i \le \varepsilon + \xi_i^*$$

$$\xi_i, \xi_i^* \ge 0, \quad i = 1 \dots l$$

For an epsilon-insensitive loss function in accordance with the invention (with different loss functions applied to censored and non-censored data), this equation becomes:

$$\min_{W,b} P_c = \frac{1}{2} W^T W + \sum_{i=1}^{l} (C_i \xi_i + C_i^* \xi_i^*) \quad (2)$$

$$\text{s.t. } y_i - (W^T \Phi(x_i) + b) \le \varepsilon_i + \xi_i$$

-continued $$(W^T \Phi(x_i) + b) - y_i \le \varepsilon_i^* + \xi_i^*$$

$$\xi_i^{(*)} \ge 0, \quad i = 1 \dots l$$

where $C_i^{(*)} = s_i C_s^{(*)} + (1 - s_i) C_n^{(*)}$ $$\varepsilon_i^{(*)} = s_i \varepsilon_s^{(*)} + (1 - s_i) \varepsilon_n^{(*)}$$

The optimization criterion penalizes data points whose y-values differ from $f(x)$ by more than $\epsilon$. The slack variables, $\xi$ and $\xi^*$, correspond to the size of this excess deviation for positive and negative deviations respectively. This penalty mechanism has two components, one for non-censored data (i.e., not right-censored) and one for censored data. Both components are, here, represented in the form of loss functions that are referred to as $\epsilon$-insensitive loss functions. An exemplary loss function 30 for censored data is defined in (3) and illustrated in FIG. 2.

$$\text{Loss}(f(x), y, s = 1) = \begin{cases} C_s^*(e - \varepsilon_s^*) & e > \varepsilon_s^* \\ 0 & -\varepsilon_s \le e \le \varepsilon_s^* \\ C_s(\varepsilon_s - e) & e < -\varepsilon_s, \end{cases} \quad (3)$$

where $e = f(x) - y$.

Thus, $e=f(x)-y$ represents the amount by which the predicted time to event differs from the actual time to event (detected/assumed event). The C and $\epsilon$ values regulate the amount of penalty incurred by various deviations between predicted and actual times to events. The C values control the slopes of the corresponding portions of the loss function 30. The positive and negative $\epsilon$ offset values ($\epsilon_s^*$ and $-\epsilon_s$) control how much deviation there is before a penalty is paid. A censored data sample is handled differently than in traditional SVR because it only provides "one-sided information." For example, in the case of survival time prediction, where $y_i$ in $z_i$ represents the survival time, a censored data sample $z_i$ only indicates that the event does not happen until $y_i$, and there is no indication of when it will happen after $y_i$, if at all. The loss function of equation (3) reflects this reality. For censored data, predicting a time to event that is before the current time (when the event has yet to happen) is worse than predicting a time that is after the current time (as this prediction may still come true). Thus, predictions for censored data are treated differently depending upon whether the prediction versus actual/current time is positive or negative. The $\epsilon$ and C values are used to differentiate the penalties incurred for f(x)>0 versus f(x)<0 (and to differentiate censored from non-censored data predictions). for predictions of time to event that are earlier than the current time, e<0, penalties are imposed for smaller deviations ($\epsilon_s < \epsilon_s^*$) than for predictions after the current time, e>0. Further, incrementally greater deviations between predictions of time to event that are earlier than the current time (and greater than $\epsilon_s$) incur incrementally larger penalties than similar differences between predictions of time that are later than the current time (and greater than $\epsilon_s^*$), that is, $C_s > C_s^*$. As a result, predictions that are before the current time incur larger penalties than predictions that are after the current time.

Figure 2:
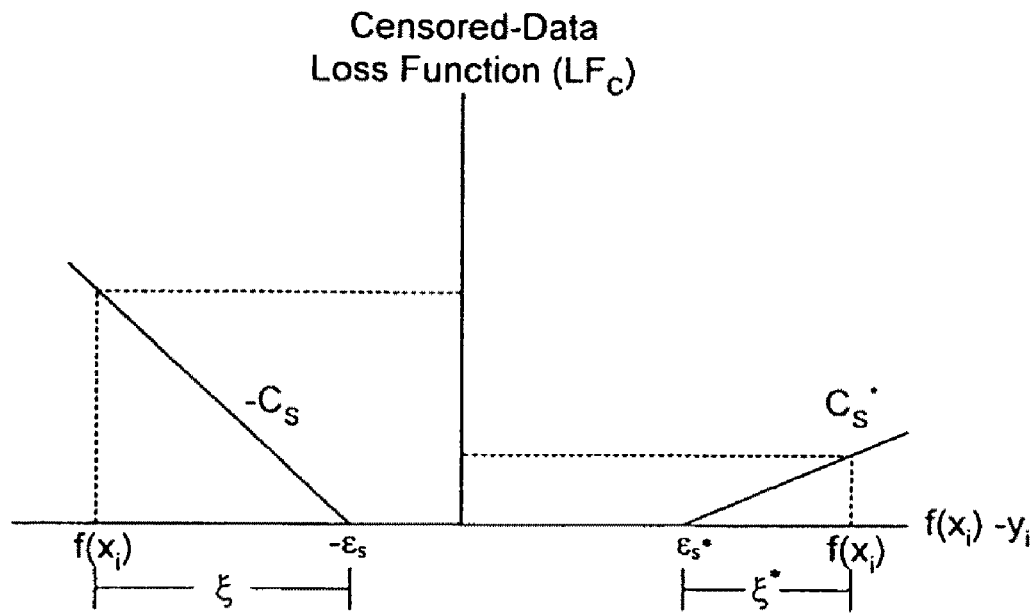
FIG. 2 is a plot of an exemplary loss function for censored data.

FIG. 2 shows that,
(1) no penalty is applied if $e \in [-\epsilon_s, 0]$; a linearly increasing penalty with a slope of $C_s$ is applied if $e \in (-\infty, -\epsilon_s)$.
(2) no penalty is applied if $e \in [0, \epsilon_s^*]$; a linearly increasing penalty with a slope of $C_s^*$ is applied if $e \in (\epsilon_s^*, \infty)$.

Because $\epsilon_s^* > \epsilon_s$ and $C_s^* < C_s$, the case where predicted value $f(x) < y$ generally incurs more penalty than the case where $f(x) > y$. This mechanism helps the resultant SVRc regression function performed by the computer 20 make full use of the one-sided information provided in the censored data sample.

Further, a modified loss function for non-censored data can also be represented in an ε-insensitive form. This loss function preferably takes into account the reality that the recorded time to event may not be the actual time to event. Although the target value $y_i$ is generally claimed to represent the time to event, $y_i$ is indeed the time when the event is detected, while the exact time the event happens is often some time before $y_i$. The computer 20 may account for this in the loss function of the non-censored data samples. An exemplary non-censored-data loss function 32 is provided in equation (4) and illustrated in FIG. 3.

$$\text{Loss}(f(x), y, s=0) = \begin{cases} C_n^*(e - \varepsilon_n^*) & e > \varepsilon_n^* \\ 0 & -\varepsilon_n \leq e \leq \varepsilon_n^* \\ C_n(\varepsilon_n - e) & e < -\varepsilon_n, \end{cases} \quad (4)$$

where $e = f(x) - y$.

Figure 3:
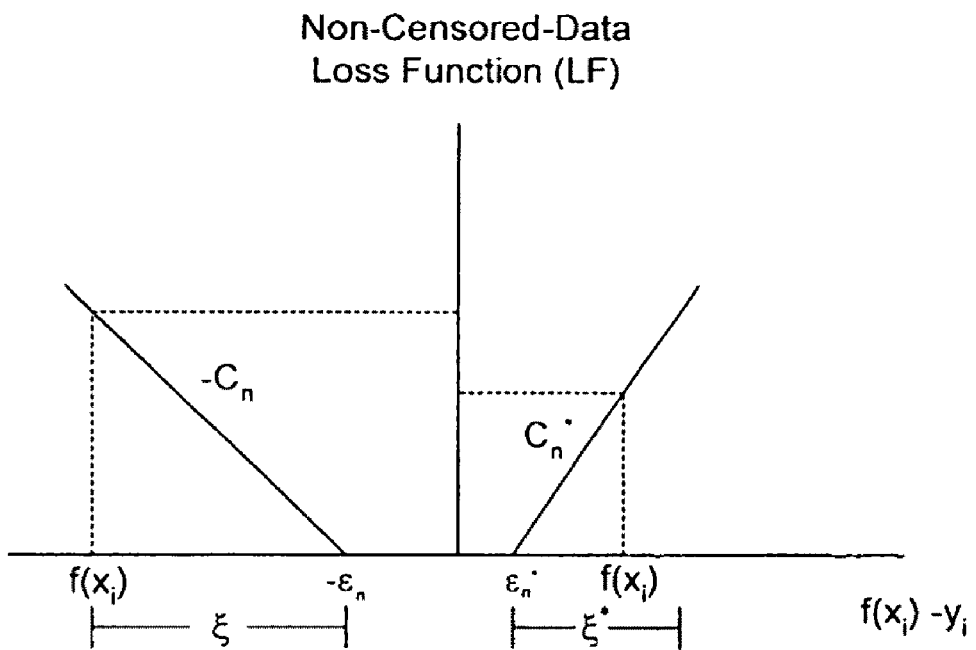
FIG. 3 is a plot of an exemplary loss function for non-censored data.

Note that $\epsilon_n^* \leq \epsilon_n$ and $C_n^* \geq C_n$, but otherwise the interpretation of FIG. 3 is generally the same as for FIG. 2.

Several simplifications and/or approximations may be made to simplify calculations. For example, because the difference between the detected event time and the exact event time is generally small, and usually negligible, $\epsilon_n^* = \epsilon_n$ and $C_n^* = C_n$ may be set, this simplifies the loss function of non-censored data samples. In order to further reduce the number of free parameters in the formulation of SVRc, and to make it easier to use, in most cases $\epsilon_s^{(*)}$, $\epsilon_n^{(*)}$, and $C_s^{(*)}$, and $C_n^{(*)}$ can be set as $\epsilon_s^* > \epsilon_s = \epsilon_n^* = \epsilon_n$ $C_s^* < C_s = C_n^* = C_n$ As is known in the art and noted above, standard SVR uses a loss function. The loss functions 30, 32 provided above are ε-insensitive loss functions, and are exemplary only, as other ε-insensitive loss functions (e.g., with different ε and/or C values), as well as other forms of loss functions, could be used. Exemplary loss functions are discussed in S. Gunn, Support Vector Machines for Classification and Regression, p. 29 (Technical Report Faculty of Engineering and Applied Science Department of Electronics and Computer Science, May 1998), which is incorporated here by reference. In addition to ε-insensitive functions, exemplary loss functions include quadratic, Laplace, or Huber loss functions. As with the loss functions 30, 32, the penalties imposed for predictions earlier versus later than the actual/current time may be different (e.g., different slopes/shapes for f(x) values below and above zero). Shapes can be used that provide for nor or essentially no penalty for ranges around f(x)=0 and provide for different incremental penalties depending upon whether f(x) is greater or less than zero.

Implementation of SVRc Construct

Figure 4:
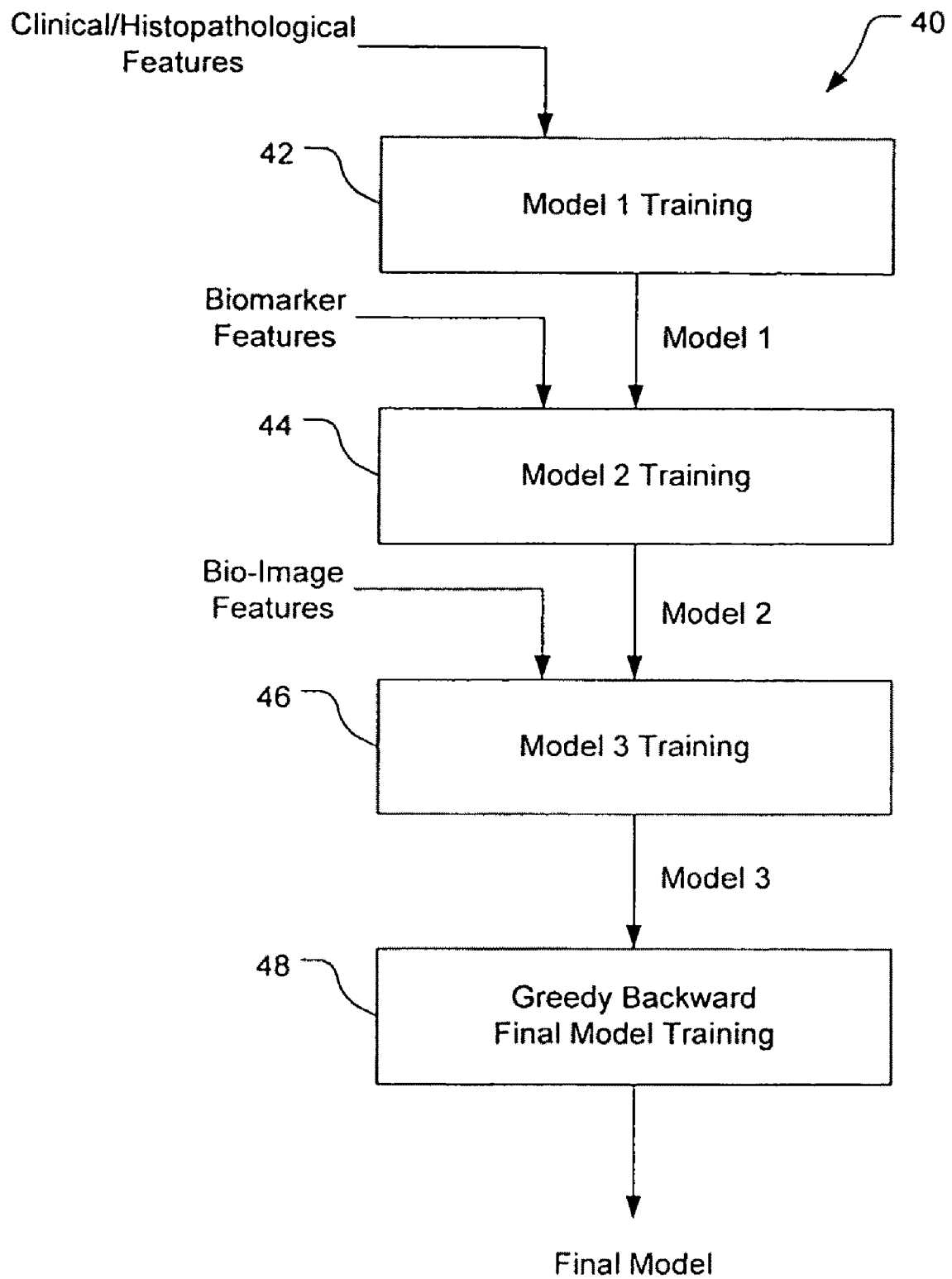
FIG. 4 is a block flow diagram of a process of developing a model for use in predicting time-to-event information.

In operation, referring to FIG. 4, with further reference to FIGS. 1-3, a process 40 for developing a predictive model using SVRc using the system 18 includes the stages shown. The process 40, however, is exemplary only and not limiting. The process 40 may be altered, e.g., by having stages added, removed, or rearranged.

At stage 42, training of an initial model, Model 1, is performed. Clinical/histopathological data 12 of corresponding clinical/histopathological features are supplied to the system 18 to determine a set of algorithm parameters and a corresponding set of model parameters for Model 1. The algorithm parameters are the parameters that govern the regression performed by the computer 20 to determine model parameters and select features. Examples of the algorithm parameters are the kernel used for the regression, and the margins $-\epsilon_s$, $\epsilon_s^*$, $-\epsilon_n$, $\epsilon_n^*$, and the loss function slopes $C_n$, $C_n^*$, $C_s$, $C_s^*$. The model parameters affect the value of the output of the model f(x) for a given input x. The algorithm parameters are set in stage 42 and are fixed at the set values for the other stages of the process 40.

Figure 5:
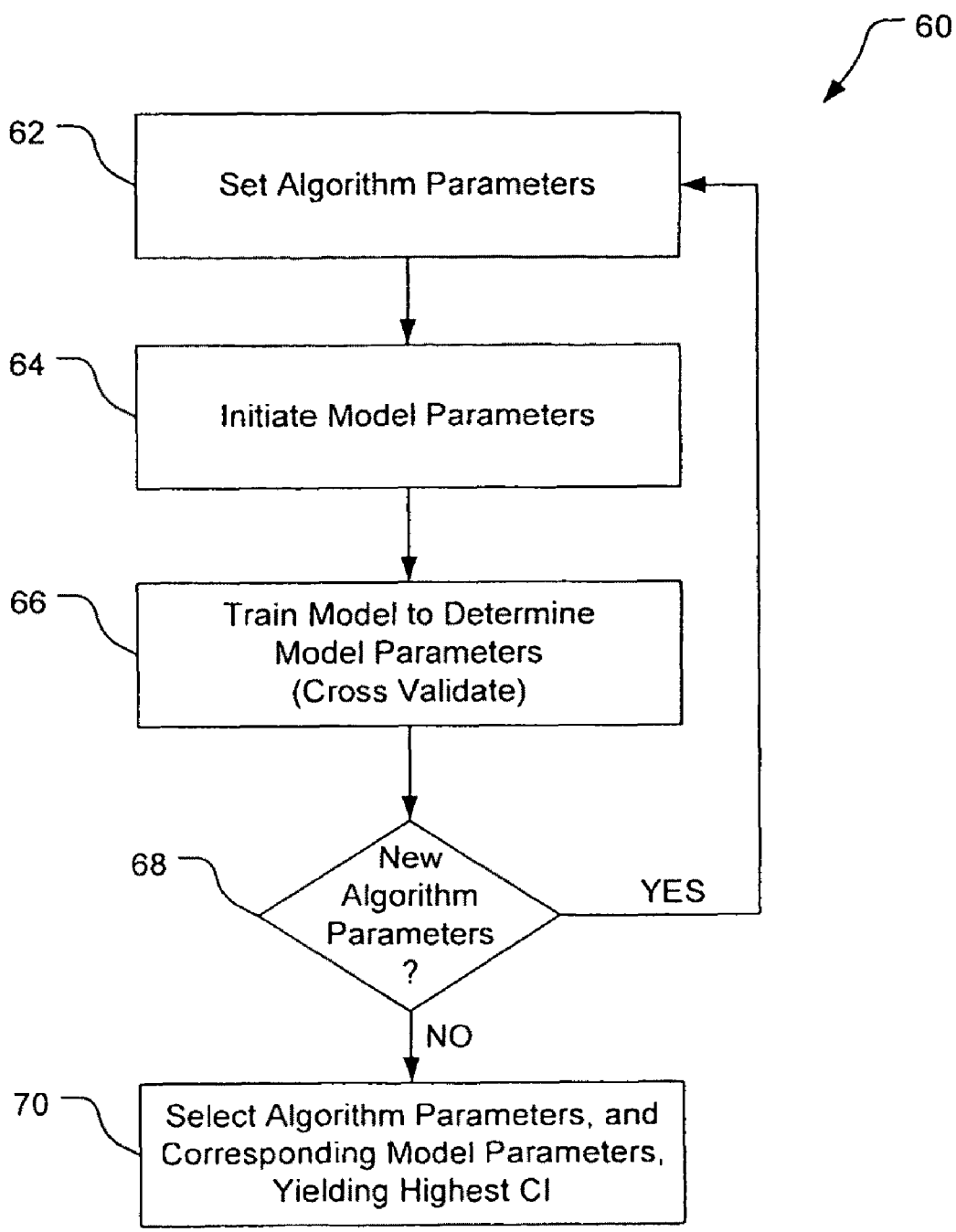
FIG. 5 is a block flow diagram of a process of producing an initial model indicated in FIG. 4.

Referring to FIG. 5, with further reference to FIGS. 1-4, a process 60 for implementing stage 42 of FIG. 4 to determine Model 1 using SVRc using the system 18 includes the stages shown. The process 60, however, is exemplary only and not limiting. The process 60 may be altered, e.g., by having stages added, removed, or rearranged.

At stage 62, algorithm parameters are initially set. The first time stage 62 is performed, the algorithm parameters are initially set, and are reset at subsequent performances of stage 62. Each time stage 62 is performed, a set of the algorithm parameters that has not been used is selected for use in the model to train model parameters.

At stage 64, model parameters are initially set. The model parameters can be a generic set of model parameter values, but are preferably based upon knowledge of SVR to reduce the time used by the computer 20 to train the model parameters. While this stage is shown separately from other stages, the actions described may be performed in conjunction with other stages, e.g., during algorithm parameter selection at stage 42 of FIG. 4 and/or stage 66.

At stage 66, model parameters are trained using the currently-selected set of algorithm parameters. To train the model parameters, portions (and possibly all of the data) of data vectors in a set of data vectors are fed into the computer 20. The data vectors comprise information associated with various features. For example, patient data vectors preferably include clinical/histopathological, biomarker, and bio-image features with corresponding values of these features for each patient. For the selecting of the algorithm parameters in the process 60, preferably only the clinical/histopathological features and corresponding values are used. These values are used as the input x in the model f to determine values of f(x). The vectors also include target values y corresponding to the target value of f(x). The computer 20 determines the values of f(x) for each patient and the difference between the model's output and the target value, f(x)–y. The computer 20 uses the loss functions 30, 32, depending upon whether the input vector x is censored or non-censored, respectively. The computer 20 uses the information from the loss functions 30, 32, in accordance with equation (2) to perform SVR to determine a set of model parameters corresponding to the current set of algorithm parameters. With model parameters determined, the computer 20 calculates and stores the concordance index (CI) for this set of algorithm parameters and model parameters using 5-fold cross-validation.

At stage 68, an inquiry is made as to whether there are more sets of algorithm parameters to try. The computer 20 determines whether each of the available sets of algorithm parameters has been used to determine a corresponding set of model parameters. If not, then the process 60 returns to stage 62 where a new set of algorithm parameters is selected. If all sets of algorithm parameters have been used to determine corresponding sets of model parameters, then the process 60 proceeds to stage 70.

At stage 70, the computer 20 selects a desired set of the algorithm parameters to use for further training of the model. The computer 20 analyzes the stored concordance indexes for the models corresponding to the various sets of algorithm parameters and associated model parameters determined by the computer 20. The computer 20 finds the maximum stored CI and fixes the corresponding algorithm parameters as the algorithm parameters that will be used for the model for the other stages of the process 40 shown in FIG. 4. This version of the model, with the selected algorithm parameters and corresponding model parameters, form Model 1. Model 1 is output from stage 42 and forms the anchor for stage 44.

Referring again to FIG. 4, with continued reference to FIGS. 1-3, at stage 44, a supplemental model, Model 2, is trained. Model 1 is used as an anchor for determining Model 2, with the algorithm parameters having been set at stage 42, which will remain the same for further model training. Model 1 is an anchor in that the features (here, clinical/histopathological features) used in Model 1 will be used in forming further models, in particular, providing the foundation for Model 2.

To form Model 2 based upon Model 1, feature selection (FS) is performed using a greedy forward (GF) algorithm, with only those features found to improve predictive accuracy of the model being kept in the model. In the exemplary context of cancer prediction, biomarker data are fed into the device 18 at stage 44 for determining which biomarker features to add to Model 1 to form Model 2. Data vectors x that now include values for the clinical/histopathological features and a selected biomarker feature are used in the SVRc construct described above. Five-fold cross-validation is used to determine model parameters with the new features included. Predictive accuracies of the revised model and the previous model are indicated by the respective CIs. If the predictive accuracy of the revised model is better than that of the immediately-previous model (for the first biomarker feature, the immediately-previous model is Model 1), then the features of the revised model are kept, and a new feature is added for evaluation. If the predictive accuracy does not improve, then the most-recently added feature is discarded, and another new feature is added for evaluation. This continues until all biomarker features have been tried and either discarded or added to the model. The model that results, with corresponding model parameters, is output by the device 18 from stage 44 as Model 2.

At stage 46, a supplemental model, Model 3, is trained. Model 2 is used as an anchor for determining Model 3. Model 2 is an anchor in that the features (here, clinical/histopathological features plus biomarker features, if any) included in Model 2 will be used in forming Model 3.

To form Model 3 based upon Model 2, feature selection (FS) is performed using a greedy forward (GF) algorithm, with only those features found to improve predictive accuracy of the model being kept in the model. Preferably, the features evaluated with respect to Model 1 to form Model 2 are, individually and/or as a group, expected to have better reliability and/or predictive power (relatedness of values of the data to the time to and/or likelihood of an event) than the features evaluated with respect to Model 2 to form Model 3. In the exemplary context of cancer prediction, bio-imaging data are fed into the device 18 at stage 46 for determining which bio-imaging features to add to Model 2 to form Model 3. Data vectors x that now include values for the clinical/histopathological features, biomarker features selected at stage 44, and a selected bio-image feature are used in the SVRc construct described above. Five-fold cross-validation is used to determine model parameters with the new feature included. Predictive accuracies of the revised model and the previous model are indicated by the respective CIs. If the predictive accuracy of the revised model is better than that of the immediately-previous model (for the first bio-image feature, the immediately-previous model is Model 2), then the feature most-recently added to the model is kept, and a new feature is added for evaluation. If the predictive accuracy does not improve, then the most-recently added feature is discarded, and another new feature is added for evaluation. This continues until all bio-imaging features have been tried and either discarded or added to the model. The model that results, with corresponding model parameters, is output by the device 18 from stage 46 as Model 3.

At stage 48, a greedy backward (GB) procedure is performed to refine the model from Model 3 to a Final Model. In performing a GB algorithm on Model 3 to perform feature selection, one feature at a time is removed from the model and the model is re-tested for its predictive accuracy. If the model's predictive accuracy increases when a feature is removed, then that feature is removed from the model and the GB process is applied to the revised model. This continues until the GB process does not yield an increase in predictive accuracy when any feature in the current feature set is removed. The Final Model parameters are then used with test data to determine the predictive accuracy of the Final Model. The resulting Final Model, with its potentially reduced feature set and determined model parameters, is the output of stage 48 and can be used by the device 18 to provide a probability of time-to-event when provided with data for the features used in the Final Model.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. Further, while in the process 60 model parameters were adjusted, model parameters may be set, e.g., based upon knowledge of SVR, and not altered thereafter. This may reduce the processing capacity and/or time to develop an SVRc model. Further still, one or more criteria may be placed upon features for them to be considered for addition to a model. For example, only features with a concordance index of a threshold value (e.g., 0.6) and above may be added to the model and tested for affect upon the model's accuracy. Thus, the feature set to be tested may be reduced, which may also reduce processing capacity and/or time for producing a model. Further still, models may be developed without using feature domains as anchors. Features may be added to the model and their impacts upon predictive accuracy considered without establishing models as anchors after each domain of features has been considered.

EXPERIMENTS AND EXPERIMENTAL RESULTS

Experiment 1

Internal Validation

Modern machine learning algorithms were applied to a 540-patient cohort of post-operative prostate cancer patients treated at Baylor University Medical Center. The patients underwent radical prostatectomy at Baylor University Medical Center. Clinical and histopathological variables were provided for 539 patients, and the number of patients missing data varied both by patient and variable. Similarly, tissue microarray slides (containing triplicate normal and triplicate tumor cores) were provided for these patients; these were used to do H&E staining for imaging, and the remaining slides were used for biomarker studies.

Regarding the image analysis component of the study, only cores that contained at least 80% tumor were used in order to preserve the integrity of the signal (and heighten the signal-to-noise ratio) attempting to be measured in these tissue samples. The signal attempting to be measured consisted of abnormalities in tumor micro-anatomy. (By contrast, the "noise" in the image analysis is the normal tissue micro-anatomical measurements.) A cutoff of 80% was chosen to simultaneously maximize the size of the cohort while preserving the integrity of the results. The effective sample size of the study, therefore, was ultimately based upon those patients who had information available from the clinical data, the biomarker data, and the bio-imaging data. Thus the total number of patients available to the integrated predictive system was 130.

SVRc was applied to this cohort of patients and their associated data. SVRc was applied to clinical/histopathological data alone (17 features), biomarker data alone (43 features from 12 markers), and bio-imaging data alone (496 features) obtained from Script 4 generated by bio-imaging software Magic (made by Aureon™ Biosciences of Yonkers, N.Y.). The SVRc algorithm was applied to each of these three types of data to find out the individual predictive capability of each data type. In each case, two models were built: one using all of the original features and the other using a set of selected features obtained by greedy-backward feature selection (SVRc-GB). The SVRc algorithm was also employed to all three types of data according to the process 40 discussed above.

Experiment 1

Results, Summary, and Conclusion

Figure 6:
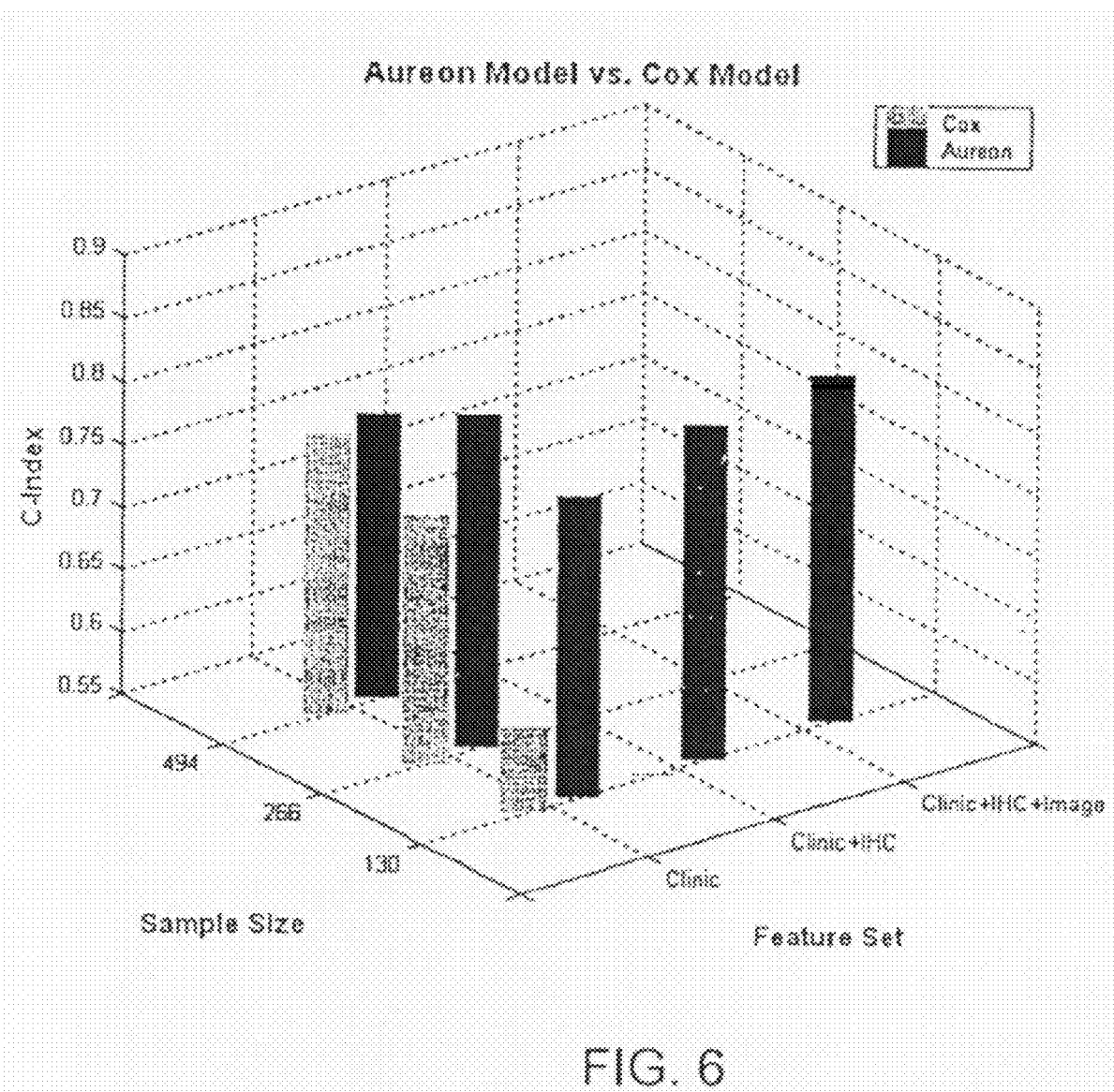
FIG. 6 is a three-dimensional graph of model performance summarized using the concordance index determined from an embodiment of the invention and from the traditional Cox proportional hazards model using experimental data.

The results are summarized in Table 1 and FIG. 6.

An incremental trend of predictive ability from the sequential addition of molecular and bio-imaging information to clinical/histopathological information alone was demonstrated. This result supports the concept that a systems pathology analysis of integrating patients' information at different levels (i.e., clinical/histopathological, micro-anatomic, and molecular) can improve the overall predictive power of the system. The analysis also demonstrated that advanced supervised multivariate modeling techniques can create improved predictive systems when compared with traditional multivariate modeling techniques. Also, in addition to the clinical/histopathological features, some molecular and bio-imaging features predictive of PSA recurrence were selected.

Advantages of SVRc were demonstrated in being able to handle high-dimensional datasets in a small cohort of patients in contrast to the benchmark conventional survival analysis method of the Cox model applied to the clinical data alone. SVRc proved solid and demonstrated better results for this study data set than those generated by the standard Cox model.

Experiment 2

Domain-Expert Knowledge External Validation

To estimate the overall system performance, a fairly conservative, two-level validation procedure was used to simulate external validation. 140 pairs of training and test sets were generated by randomly picking 100 records as the training set and using the remaining 30 records not selected as the test set.
(1) For each pair, the training set was used to build a predictive model using the process 40.
(2) The built model was then applied to the test set to estimate the Final Model's predictive accuracy.
(3) Steps (1) and (2) were repeated 40 times to get 40 predictive accuracies and the final predictive performance was reported as the average predictive accuracy over the 40 distinct Final Models.

The most-frequently selected features in the 40 different Final Models above were then used to train three additional models for each pair of training and testing sets using SVRc: a model based on clinical/pathological features alone; a model based on the clinical/pathological features and the biomarker features; and the model based on the clinical/pathological/biomarker features and the bio-imaging feature.

Experiment 2

Results, Summary, and Conclusion

The experimental results are illustrated in Table 2. The results can be summarized as follows:

For the 40 runs, the average generalization accuracy (i.e., predictive accuracy of the model when applied to a test set) was:
(1) 0.74 for clinical/histopathological data alone;
(2) 0.76 for clinical/histopathological plus biomarker information; and
(3) 0.77 for clinical/histopathological/biomarker plus bio-imaging data.

The full list of features and the frequency with which they were kept in the final model is provided in the Appendix.

As before, an incremental trend of predictive ability from the sequential addition of molecular and bio-imaging information to clinical/histopathological information alone was demonstrated. This result further supports the concept that a systems pathology analysis of integrating patients' information at different levels (i.e., clinical/histopathological, micro-anatomic, and molecular) can improve the overall predictive power of the system. The analysis also again demonstrated that advanced supervised multivariate modeling techniques can create improved predictive systems when compared with traditional multivariate modeling techniques in handling high-dimensional datasets in a small cohort of patients, here applied to the clinical data alone.

It can also be concluded that adding a layer of domain expertise can assist in selecting features that improve the predictive ability of the system.

Appendix

| Clinical & Histopathological Features | Description | |
|---|---|---|
| pldy.rslt.cd | Ploidy: diploid, tetraploid, aneuploid | 39 |
| pldy.pct.s.phase | Ploidy: percent in S phase | 40 |
| pldy.prolif.fractn | Ploidy proliferation fraction | 32 |
| AGE | Age (in years) | 35 |
| RACE | Race | 28 |
| BXGG1 | Dominant biopsy Gleason score | 38 |
| BXGGTOT | Biopsy Gleason grade | 39 |
| PREPSA | Preoperative PSA (prostate-specific antigen) | 35 |
| DRE | Palpable on DRE (digital rectal exam) | 39 |
| UICC | UICC clinical stage | 38 |

-continued

| Clinical & Histopathological Features | Description | |
|---|---|---|
| LN | Lymph node status | 35 |
| MARGINS | Surgical margin status | 31 |
| ECE | Extracapsular Invasion | 23 |
| SVI | Seminal vesicle invasion | 39 |
| GG1 | Dominant prostatectomy Gleason score | 35 |
| GGTOT | Prostatectomy Gleason grade | 36 |

| Biomarker Features | Description | |
|---|---|---|
| ATKI67T1 | Ki67 in intensity area 1 (tumor) | 5 |
| ATKI67T2 | Ki67 in intensity area 2 (tumor) | 7 |
| ATKI67T3 | Ki67 in intensity area 3 (tumor) | 6 |
| ATKI67P1 | Ki67 in intensity area 1 (PIN) | 3 |
| ATKI67P2 | Ki67 in intensity area 2 (PIN) | 3 |
| ATKI67P3 | Ki67 in intensity area 3 (PIN) | 2 |
| ATKI67A1 | Ki67 in intensity area 1 (gland) | 1 |
| ATKI67A2 | Ki67 in intensity area 2 (gland) | 1 |
| ATKI67A3 | Ki67 in intensity area 3 (gland) | 0 |
| ATC18T3 | c18 (tumor) | 0 |
| ATCD45T3 | cd45 (tumor) | 4 |
| ATCD68T3 | cd68 (tumor) | 4 |
| ATCD34P | cd34 (PIN) | 0 |
| ATCD34S | cd34 (stroma) | 3 |
| ATCD34T | cd34 (tumor) | 2 |
| ATCD34TP | cd34 (tumor/PIN) | 5 |
| ATCD34TS | cd34 (tumor/stroma) | 4 |
| ATCD34PS | cd34 (PIN/stroma) | 4 |
| ATC18P3 | c18 (PIN) | 0 |
| ATCD45P3 | cd45 (PIN) | 3 |
| ATC18A3 | c18 (gland) | 0 |
| ATCD45A3 | cd45 (gland) | 0 |
| ARSI | AR staining index (tumor) | 33 |
| C14SI | cytokeratin 14 staining index (tumor) | 1 |
| CD1SI | cyclin-D1 staining index (tumor) | 2 |
| PSASI | PSA staining index (tumor) | 4 |
| PSMASI | PSMA staining index (tumor) | 1 |
| P27SI | p27 staining index (tumor) | 2 |
| HER2SI | her2/neu staining index (tumor) | 7 |
| ARPSI | AR staining index (PIN) | 3 |
| C14PSI | cytokeratin 14 staining index (PIN) | 7 |
| CD1PSI | cyclin-D1 staining index (PIN) | 0 |
| PSAPSI | PSA staining index (PIN) | 5 |
| PSMAPSI | PSMA staining index (PIN) | 1 |
| P27PSI | p27 staining index (PIN) | 1 |
| HER2PSI | her2/neu staining index (PIN) | 0 |
| ARASI | AR staining index (gland) | 22 |
| C14ASI | cytokeratin 14 staining index (gland) | 0 |
| CD1ASI | cyclin-D1 staining index (gland) | 0 |
| PSAASI | PSA staining index (gland) | 5 |
| PSMAASI | PSMA staining index (gland) | 1 |
| P27ASI | p27 staining index (gland) | 3 |
| HER2ASI | her2/neu staining index (gland) | 0 |

| Bio-imaging Features | |
|---|---|
| Background.MaxAreaPxl | 3 |
| Background.MeanAreaPxl | 0 |
| Background.MinAreaPxl | 0 |
| Background.StdDevAreaPxl | 6 |
| Background.SumAreaPxl | 0 |
| Cytoplasm.Objects | 2 |
| Cytoplasm.ObjectsPct | 1 |
| Cytoplasm.MaxAreaPxl | 0 |
| Cytoplasm.MeanAreaPxl | 2 |
| Cytoplasm.MinAreaPxl | 1 |
| Cytoplasm.StdDevAreaPxl | 1 |
| Cytoplasm.SumAreaPxl | 1 |
| Cytoplasm.MaxAsymmetry | 0 |

-continued

| Bio-imaging Features | |
|---|---|
| Cytoplasm.MeanAsymmetry | 0 |
| Cytoplasm.MinAsymmetry | 2 |
| Cytoplasm.StdDevAsymmetry | 0 |
| Cytoplasm.MaxBorderlengthm | 0 |
| Cytoplasm.MeanBorderlengthm | 0 |
| Cytoplasm.MinBorderlengthm | 2 |
| Cytoplasm.StdDevBorderlengthm | 0 |
| Cytoplasm.SumBorderlengthm | 0 |
| Cytoplasm.MaxBrightness | 0 |
| Cytoplasm.MeanBrightness | 0 |
| Cytoplasm.MinBrightness | 0 |
| Cytoplasm.StdDevBrightness | 1 |
| Cytoplasm.MaxCompactness | 1 |
| Cytoplasm.MeanCompactness | 0 |
| Cytoplasm.MinCompactness | 2 |
| Cytoplasm.StdDevCompactness | 0 |
| Cytoplasm.MaxDensity | 0 |
| Cytoplasm.MeanDensity | 1 |
| Cytoplasm.MinDensity | 0 |
| Cytoplasm.StdDevDensity | 1 |
| Cytoplasm.MaxDiff.ofenclosing.enclo | 2 |
| Cytoplasm.MeanDiff.ofenclosing.encl | 0 |
| Cytoplasm.MinDiff.ofenclosing.enclo | 0 |
| Cytoplasm.StdDevDiff.ofenclosing.en | 1 |
| Cytoplasm.MaxEllipticFit | 0 |
| Cytoplasm.MeanEllipticFit | 0 |
| Cytoplasm.MinEllipticFit | 0 |
| Cytoplasm.StdDevEllipticFit | 1 |
| Cytoplasm.MaxLengthm | 0 |
| Cytoplasm.MeanLengthm | 0 |
| Cytoplasm.MinLengthm | 0 |
| Cytoplasm.StdDevLengthm | 0 |
| Cytoplasm.SumLengthm | 0 |
| Cytoplasm.MaxMax.Diff. | 1 |
| Cytoplasm.MeanMax.Diff. | 0 |
| Cytoplasm.MinMax.Diff. | 1 |
| Epithelial.Nuclei.MaxRadiusofsmalle | 0 |
| Epithelial.Nuclei.MeanRadiusofsmall | 0 |
| Epithelial.Nuclei.MinRadiusofsmalle | 0 |
| Epithelial.Nuclei.StdDevRadiusofsma | 0 |
| Epithelial.Nuclei.MaxStdevChannel1 | 0 |
| Epithelial.Nuclei.MeanStdevChannel1 | 0 |
| Epithelial.Nuclei.MinStdevChannel1 | 1 |
| Epithelial.Nuclei.StdDevStdevChanne | 0 |
| Epithelial.Nuclei.MaxStdevChannel2 | 3 |
| Epithelial.Nuclei.MeanStdevChannel2 | 0 |
| Epithelial.Nuclei.MinStdevChannel2 | 0 |
| Epithelial.Nuclei.StdDevStdevChannel3 | 0 |
| Epithelial.Nuclei.MaxStdevChannel3 | 0 |
| Epithelial.Nuclei.MeanStdevChannel3 | 0 |
| Epithelial.Nuclei.MinStdevChannel3 | 2 |
| Epithelial.Nuclei.StdDevStdevChanne4 | 0 |
| Epithelial.Nuclei.MaxWidthm | 0 |
| Epithelial.Nuclei.MeanWidthm | 0 |
| Epithelial.Nuclei.MinWidthm | 1 |
| Epithelial.Nuclei.StdDevWidthm | 0 |
| Lumen.Objects | 1 |
| Lumen.ObjectsPct | 1 |
| Lumen.MaxAreaPxl | 1 |
| Lumen.MeanAreaPxl | 0 |
| Lumen.MinAreaPxl | 0 |
| Lumen.StdDevAreaPxl | 4 |
| Lumen.SumAreaPxl | 2 |
| Lumen.MaxAsymmetry | 0 |
| Lumen.MeanAsymmetry | 0 |
| Lumen.MinAsymmetry | 0 |
| Lumen.StdDevAsymmetry | 1 |
| Lumen.MaxBorderlengthm | 10 |
| Lumen.MeanBorderlengthm | 1 |
| Lumen.MinBorderlengthm | 0 |
| Lumen.StdDevBorderlengthm | 5 |
| Lumen.SumBorderlengthm | 5 |
| Lumen.MaxBrightness | 0 |
| Lumen.MeanBrightness | 1 |
| Lumen.MinBrightness | 0 |
| Lumen.StdDevBrightness | 0 |
| Lumen.MaxCompactness | 0 |
| Lumen.MeanCompactness | 0 |

| Bio-imaging Features | |
|---|---|
| Lumen.MinCompactness | 4 |
| Lumen.StdDevCompactness | 0 |
| Lumen.MaxDensity | 0 |
| Lumen.MeanDensity | 0 |
| Lumen.MinDensity | 1 |
| Lumen.StdDevDensity | 2 |
| Lumen.MaxDiff.ofenclosing.enclosede | 0 |
| Red.Blood.Cell.MeanMeanChannel1 | 0 |
| Red.Blood.Cell.MinMeanChannel1 | 0 |
| Red.Blood.Cell.StdDevMeanChannel1 | 0 |
| Red.Blood.Cell.MaxMeanChannel2 | 1 |
| Red.Blood.Cell.MeanMeanChannel2 | 0 |
| Red.Blood.Cell.MinMeanChannel2 | 0 |
| Red.Blood.Cell.StdDevMeanChannel2 | 0 |
| Red.Blood.Cell.MaxMeanChannel3 | 0 |
| Red.Blood.Cell.MeanMeanChannel3 | 0 |
| Red.Blood.Cell.MinMeanChannel3 | 0 |
| Red.Blood.Cell.StdDevMeanChannel3 | 0 |
| Red.Blood.Cell.MaxRadiusoflargesten | 0 |
| Red.Blood.Cell.MeanRadiusoflargeste | 0 |
| Red.Blood.Cell.MinRadiusoflargesten | 1 |
| Red.Blood.Cell.StdDevRadiusoflarges | 0 |
| Red.Blood.Cell.MaxRadiusofsmalleste | 1 |
| Red.Blood.Cell.MeanRadiusofsmallest | 0 |
| Red.Blood.Cell.MinRadiusofsmalleste | 0 |
| Red.Blood.Cell.StdDevRadiusofsmalle | 1 |
| Red.Blood.Cell.MaxStdevChannel1 | 0 |
| Red.Blood.Cell.MeanStdevChannel1 | 0 |
| Red.Blood.Cell.MinStdevChannel1 | 0 |
| Red.Blood.Cell.StdDevStdevChannel1 | 0 |
| Red.Blood.Cell.MaxStdevChannel2 | 0 |
| Red.Blood.Cell.MeanStdevChannel2 | 1 |
| Red.Blood.Cell.MinStdevChannel2 | 0 |
| Red.Blood.Cell.StdDevStdevChannel2 | 0 |
| Red.Blood.Cell.MaxStdevChannel3 | 0 |
| Red.Blood.Cell.MeanStdevChannel3 | 0 |
| Red.Blood.Cell.MinStdevChannel3 | 0 |
| Red.Blood.Cell.StdDevStdevChannel3 | 1 |
| Red.Blood.Cell.MaxWidthm | 1 |
| Red.Blood.Cell.MeanWidthm | 0 |
| Red.Blood.Cell.MinWidthm | 0 |
| Red.Blood.Cell.StdDevWidthm | 0 |
| Stroma.Objects | 0 |
| Stroma.ObjectsPct | 0 |
| Stroma.MaxAreaPxl | 1 |
| Stroma.MeanAreaPxl | 0 |
| Stroma.MinAreaPxl | 2 |
| Stroma.StdDevAreaPxl | 0 |
| Stroma.SumAreaPxl | 0 |
| Stroma.MaxAsymmetry | 0 |
| Stroma.MeanAsymmetry | 0 |
| Stroma.MinAsymmetry | 0 |
| Stroma.StdDevAsymmetry | 1 |
| Stroma.MaxBorderlengthm | 1 |
| Stroma.MeanBorderlengthm | 1 |
| Stroma.MinBorderlengthm | 1 |
| Stroma.Nuclei.StdDevDiff.ofenclosin | 0 |
| Stroma.Nuclei.MaxEllipticFit | 0 |
| Stroma.Nuclei.MeanEllipticFit | 1 |
| Stroma.Nuclei.MinEllipticFit | 1 |
| Stroma.Nuclei.StdDevEllipticFit | 0 |
| Stroma.Nuclei.MaxLengthm | 0 |
| Stroma.Nuclei.MeanLengthm | 0 |
| Stroma.Nuclei.MinLengthm | 0 |
| Stroma.Nuclei.StdDevLengthm | 1 |
| Stroma.Nuclei.SumLengthm | 0 |
| Stroma.Nuclei.MaxMax.Diff. | 0 |
| Stroma.Nuclei.MeanMax.Diff. | 0 |
| Stroma.Nuclei.MinMax.Diff. | 0 |
| Stroma.Nuclei.StdDevMax.Diff. | 0 |
| Stroma.Nuclei.MaxMeanChannel1 | 0 |
| Stroma.Nuclei.MeanMeanChannel1 | 0 |
| Stroma.Nuclei.MinMeanChannel1 | 0 |
| Stroma.Nuclei.StdDevMeanChannel1 | 0 |
| Stroma.Nuclei.MaxMeanChannel2 | 0 |
| Stroma.Nuclei.MeanMeanChannel2 | 0 |
| Stroma.Nuclei.MinMeanChannel2 | 0 |
| Stroma.Nuclei.StdDevMeanChannel2 | 0 |
| Stroma.Nuclei.MaxMeanChannel3 | 0 |
| Stroma.Nuclei.MeanMeanChannel3 | 0 |
| Stroma.Nuclei.MinMeanChannel3 | 0 |
| Stroma.Nuclei.StdDevMeanChannel3 | 0 |
| Stroma.Nuclei.MaxRadiusoflargestenc | 0 |
| Stroma.Nuclei.MeanRadiusoflargesten | 0 |
| Stroma.Nuclei.MinRadiusoflargestenc | 0 |
| Stroma.Nuclei.StdDevRadiusoflargest | 0 |
| Stroma.Nuclei.MaxRadiusofsmallesten | 0 |
| Stroma.Nuclei.MeanRadiusofsmalleste | 1 |
| Stroma.Nuclei.MinRadiusofsmallesten | 0 |
| Stroma.Nuclei.StdDevRadiusofsmalles | 0 |
| Stroma.Nuclei.MaxStdevChannel1 | 0 |
| Stroma.Nuclei.MeanStdevChannel1 | 0 |
| Stroma.Nuclei.MinStdevChannel1 | 1 |
| Stroma.Nuclei.StdDevStdevChannel1 | 0 |
| Stroma.Nuclei.MaxStdevChannel2 | 0 |
| Stroma.Nuclei.MeanStdevChannel2 | 1 |
| Stroma.Nuclei.MinStdevChannel2 | 0 |
| Stroma.Nuclei.StdDevStdevChannel2 | 0 |
| Stroma.Nuclei.MaxStdevChannel3 | 0 |
| Stroma.Nuclei.MeanStdevChannel3 | 0 |
| Stroma.Nuclei.MinStdevChannel3 | 1 |
| Stroma.Nuclei.StdDevStdevChannel3 | 0 |
| Cytoplasm.StdDevMax.Diff. | 0 |
| Cytoplasm.MaxMeanChannel1 | 0 |
| Cytoplasm.MeanMeanChannel1 | 1 |
| Cytoplasm.MinMeanChannel1 | 0 |
| Cytoplasm.StdDevMeanChannel1 | 0 |
| Cytoplasm.MaxMeanChannel2 | 1 |
| Cytoplasm.MeanMeanChannel2 | 0 |
| Cytoplasm.MinMeanChannel2 | 1 |
| Cytoplasm.StdDevMeanChannel2 | 0 |
| Cytoplasm.MaxMeanChannel3 | 0 |
| Cytoplasm.MeanMeanChannel3 | 0 |
| Cytoplasm.MinMeanChannel3 | 0 |
| Cytoplasm.StdDevMeanChannel3 | 0 |
| Cytoplasm.MaxRadiusoflargestenclose | 0 |
| Cytoplasm.MeanRadiusoflargestenclos | 0 |
| Cytoplasm.MinRadiusoflargestenclose | 0 |
| Cytoplasm.StdDevRadiusoflargestencl | 0 |
| Cytoplasm.MaxRadiusofsmallestenclos | 1 |
| Cytoplasm.MeanRadiusofsmallestenclo | 0 |
| Cytoplasm.MinRadiusofsmallestenclos | 0 |
| Cytoplasm.StdDevRadiusofsmallestenc | 1 |
| Cytoplasm.MaxStdevChannel1 | 0 |
| Cytoplasm.MeanStdevChannel1 | 0 |
| Cytoplasm.MinStdevChannel1 | 0 |
| Cytoplasm.StdDevStdevChannel1 | 0 |
| Cytoplasm.MaxStdevChannel2 | 2 |
| Cytoplasm.MeanStdevChannel2 | 0 |
| Cytoplasm.MinStdevChannel2 | 1 |
| Cytoplasm.StdDevStdevChannel2 | 0 |
| Cytoplasm.MaxStdevChannel3 | 0 |
| Cytoplasm.MeanStdevChannel3 | 0 |
| Cytoplasm.MinStdevChannel3 | 1 |
| Cytoplasm.StdDevStdevChannel3 | 0 |
| Cytoplasm.MaxWidthm | 1 |
| Cytoplasm.MeanWidthm | 3 |
| Cytoplasm.MinWidthm | 0 |
| Cytoplasm.StdDevWidthm | 0 |
| Epithelial.Nuclei.Objects | 0 |
| Epithelial.Nuclei.ObjectsPct | 0 |
| Epithelial.Nuclei.MaxAreaPxl | 0 |
| Epithelial.Nuclei.MeanAreaPxl | 0 |
| Epithelial.Nuclei.MinAreaPxl | 1 |
| Epithelial.Nuclei.StdDevAreaPxl | 2 |
| Epithelial.Nuclei.SumAreaPxl | 0 |
| Epithelial.Nuclei.MaxAsymmetry | 0 |
| Epithelial.Nuclei.MeanAsymmetry | 0 |
| Epithelial.Nuclei.MinAsymmetry | 1 |
| Epithelial.Nuclei.StdDevAsymmetry | 2 |
| Epithelial.Nuclei.MaxBorderlengthm | 0 |
| Lumen.MeanDiff.ofenclosing.enclosed | 0 |
| Lumen.MinDiff.ofenclosing.enclosede | 0 |
| Lumen.StdDevDiff.ofenclosing.enclos | 1 |
| Lumen.MaxEllipticFit | 2 |
| Lumen.MeanEllipticFit | 0 |

-continued

| Bio-imaging Features | |
|---|---|
| Lumen.MinEllipticFit | 1 |
| Lumen.StdDevEllipticFit | 1 |
| Lumen.MaxLengthm | 1 |
| Lumen.MeanLengthm | 1 |
| Lumen.MinLengthm | 0 |
| Lumen.StdDevLengthm | 0 |
| Lumen.SumLengthm | 0 |
| Lumen.MaxMax.Diff. | 0 |
| Lumen.MeanMax.Diff. | 0 |
| Lumen.MinMax.Diff. | 0 |
| Lumen.StdDevMax.Diff. | 0 |
| Lumen.MaxMeanChannel1 | 0 |
| Lumen.MeanMeanChannel1 | 0 |
| Lumen.MinMeanChannel1 | 2 |
| Lumen.StdDevMeanChannel1 | 0 |
| Lumen.MaxMeanChannel2 | 0 |
| Lumen.MeanMeanChannel2 | 0 |
| Lumen.MinMeanChannel2 | 0 |
| Lumen.StdDevMeanChannel2 | 0 |
| Lumen.MaxMeanChannel3 | 0 |
| Lumen.MeanMeanChannel3 | 0 |
| Lumen.MinMeanChannel3 | 0 |
| Lumen.StdDevMeanChannel3 | 0 |
| Lumen.MaxRadiusoflargestenclosedell | 0 |
| Lumen.MeanRadiusoflargestenclosedel | 0 |
| Lumen.MinRadiusoflargestenclosedell | 0 |
| Lumen.StdDevRadiusoflargestenclosed | 1 |
| Lumen.MaxRadiusofsmallestenclosinge | 0 |
| Lumen.MeanRadiusofsmallestenclosing | 0 |
| Lumen.MinRadiusofsmallestenclosinge | 6 |
| Lumen.StdDevRadiusofsmallestenclosi | 0 |
| Lumen.MaxStdevChannel1 | 0 |
| Lumen.MeanStdevChannel1 | 0 |
| Lumen.MinStdevChannel1 | 0 |
| Lumen.StdDevStdevChannel1 | 1 |
| Lumen.MaxStdevChannel2 | 0 |
| Lumen.MeanStdevChannel2 | 0 |
| Lumen.MinStdevChannel2 | 0 |
| Lumen.StdDevStdevChannel2 | 0 |
| Lumen.MaxStdevChannel3 | 0 |
| Lumen.MeanStdevChannel3 | 1 |
| Lumen.MinStdevChannel3 | 0 |
| Lumen.StdDevStdevChannel3 | 0 |
| Lumen.MaxWidthm | 0 |
| Stroma.StdDevBorderlengthm | 0 |
| Stroma.SumBorderlengthm | 0 |
| Stroma.MaxBrightness | 2 |
| Stroma.MeanBrightness | 0 |
| Stroma.MinBrightness | 0 |
| Stroma.StdDevBrightness | 0 |
| Stroma.MaxCompactness | 0 |
| Stroma.MeanCompactness | 0 |
| Stroma.MinCompactness | 0 |
| Stroma.StdDevCompactness | 0 |
| Stroma.MaxDensity | 1 |
| Stroma.MeanDensity | 0 |
| Stroma.MinDensity | 0 |
| Stroma.StdDevDensity | 0 |
| Stroma.MaxDiff.ofenclosing.enclosed | 2 |
| Stroma.MeanDiff.ofenclosing.enclose | 0 |
| Stroma.MinDiff.ofenclosing.enclosed | 0 |
| Stroma.StdDevDiff.ofenclosing.enclo | 0 |
| Stroma.MaxEllipticFit | 0 |
| Stroma.MeanEllipticFit | 0 |
| Stroma.MinEllipticFit | 0 |
| Stroma.StdDevEllipticFit | 0 |
| Stroma.MaxLengthm | 0 |
| Stroma.MeanLengthm | 0 |
| Stroma.MinLengthm | 0 |
| Stroma.StdDevLengthm | 0 |
| Stroma.SumLengthm | 0 |
| Stroma.MaxMax.Diff. | 0 |
| Stroma.MeanMax.Diff. | 0 |
| Stroma.MinMax.Diff. | 0 |
| Stroma.StdDevMax.Diff. | 2 |
| Stroma.MaxMeanChannel1 | 0 |
| Stroma.MeanMeanChannel1 | 0 |
| Stroma.MinMeanChannel1 | 0 |

-continued

| Bio-imaging Features | |
|---|---|
| Stroma.StdDevMeanChannel1 | 0 |
| Stroma.MaxMeanChannel2 | 0 |
| Stroma.MeanMeanChannel2 | 0 |
| Stroma.MinMeanChannel2 | 0 |
| Stroma.StdDevMeanChannel2 | 0 |
| Stroma.MaxMeanChannel3 | 0 |
| Stroma.MeanMeanChannel3 | 0 |
| Stroma.MinMeanChannel3 | 0 |
| Stroma.StdDevMeanChannel3 | 0 |
| Stroma.MaxRadiusoflargestenclosedel | 0 |
| Stroma.MeanRadiusoflargestenclosede | 0 |
| Stroma.MinRadiusoflargestenclosedel | 0 |
| Stroma.StdDevRadiusoflargestenclose | 0 |
| Stroma.MaxRadiusofsmallestenclosing | 0 |
| Stroma.Nuclei.MaxWidthm | 0 |
| Stroma.Nuclei.MeanWidthm | 0 |
| Stroma.MeanRadiusofsmallestenclosin | 0 |
| Stroma.Nuclei.StdDevWidthm | 0 |
| Stroma.Nuclei.MinWidthm | 1 |
| Stroma.Nuclei.MinDiff.ofenclosing.e | 0 |
| AK.1.C2EN | 0 |
| AK.2.EN2SN | 0 |
| AK.3.L2Core | 1 |
| AK.4.C2L | 0 |
| AK.5.CEN2L | 0 |
| Epithelial.Nuclei.MeanBorderlengthm | 0 |
| Epithelial.Nuclei.MinBorderlengthm | 2 |
| Epithelial.Nuclei.StdDevBorderlengt | 1 |
| Epithelial.Nuclei.SumBorderlengthm | 0 |
| Epithelial.Nuclei.MaxBrightness | 0 |
| Epithelial.Nuclei.MeanBrightness | 0 |
| Epithelial.Nuclei.MinBrightness | 0 |
| Epithelial.Nuclei.StdDevBrightness | 0 |
| Epithelial.Nuclei.MaxCompactness | 5 |
| Epithelial.Nuclei.MeanCompactness | 0 |
| Epithelial.Nuclei.MinCompactness | 0 |
| Epithelial.Nuclei.StdDevCompactness | 1 |
| Epithelial.Nuclei.MaxDensity | 0 |
| Epithelial.Nuclei.MeanDensity | 0 |
| Epithelial.Nuclei.MeanDensity | 2 |
| Epithelial.Nuclei.StdDevDensity | 0 |
| Epithelial.Nuclei.MaxDiff.ofenclosi | 1 |
| Epithelial.Nuclei.MeanDiff.ofenclos | 0 |
| Epithelial.Nuclei.MinDiff.ofenclosi | 0 |
| Epithelial.Nuclei.StdDevDiff.ofencl | 2 |
| Epithelial.Nuclei.MaxEllipticFit | 0 |
| Epithelial.Nuclei.MeanEllipticFit | 0 |
| Epithelial.Nuclei.MinEllipticFit | 0 |
| Epithelial.Nuclei.StdDevEllipticFit | 0 |
| Epithelial.Nuclei.MaxLengthm | 1 |
| Epithelial.Nuclei.MeanLengthm | 0 |
| Epithelial.Nuclei.MinLengthm | 0 |
| Epithelial.Nuclei.StdDevLengthm | 2 |
| Epithelial.Nuclei.SumLengthm | 0 |
| Epithelial.Nuclei.MaxMax.Diff. | 0 |
| Epithelial.Nuclei.MeanMax.Diff. | 1 |
| Epithelial.Nuclei.MinMax.Diff. | 1 |
| Epithelial.Nuclei.StdDevMax.Diff. | 0 |
| Epithelial.Nuclei.MaxMeanChannel1 | 1 |
| Epithelial.Nuclei.MeanMeanChannel1 | 0 |
| Epithelial.Nuclei.MinMeanChannel1 | 1 |
| Epithelial.Nuclei.StdDevMeanChannel | 0 |
| Epithelial.Nuclei.MaxMeanChannel2 | 0 |
| Epithelial.Nuclei.MeanMeanChannel2 | 0 |
| Epithelial.Nuclei.MinMeanChannel2 | 0 |
| Epithelial.Nuclei.StdDevMeanChannel1 | 1 |
| Epithelial.Nuclei.MaxMeanChannel3 | 1 |
| Epithelial.Nuclei.MeanMeanChannel3 | 0 |
| Epithelial.Nuclei.MinMeanChannel3 | 0 |
| Epithelial.Nuclei.StdDevMeanChannel2 | 0 |
| Epithelial.Nuclei.MaxRadiusoflarges | 0 |
| Epithelial.Nuclei.MeanRadiusoflarge | 1 |
| Epithelial.Nuclei.MinRadiusoflarges | 0 |
| Epithelial.Nuclei.StdDevRadiusoflar | 0 |
| Lumen.MeanWidthm | 0 |
| Lumen.MinWidthm | 0 |
| Lumen.StdDevWidthm | 1 |
| Red.Blood.Cell.Objects | 0 |

| Bio-imaging Features | |
| --- | --- |
| Red.Blood.Cell.ObjectsPct | 1 |
| Red.Blood.Cell.MaxAreaPxl | 1 |
| Red.Blood.Cell.MeanAreaPxl | 0 |
| Red.Blood.Cell.MinAreaPxl | 1 |
| Red.Blood.Cell.StdDevAreaPxl | 3 |
| Red.Blood.Cell.SumAreaPxl | 0 |
| Red.Blood.Cell.MaxAsymmetry | 0 |
| Red.Blood.Cell.MeanAsymmetry | 0 |
| Red.Blood.Cell.MinAsymmetry | 0 |
| Red.Blood.Cell.StdDevAsymmetry | 0 |
| Red.Blood.Cell.MaxBorderlengthm | 0 |
| Red.Blood.Cell.MeanBorderlengthm | 0 |
| Red.Blood.Cell.MinBorderlengthm | 1 |
| Red.Blood.Cell.StdDevBorderlengthm | 1 |
| Red.Blood.Cell.SumBorderlengthm | 0 |
| Red.Blood.Cell.MaxBrightness | 0 |
| Red.Blood.Cell.MeanBrightness | 0 |
| Red.Blood.Cell.MinBrightness | 1 |
| Red.Blood.Cell.StdDevBrightness | 0 |
| Red.Blood.Cell.MaxCompactness | 0 |
| Red.Blood.Cell.MeanCompactness | 0 |
| Red.Blood.Cell.MinCompactness | 0 |
| Red.Blood.Cell.StdDevCompactness | 1 |
| Red.Blood.Cell.MaxDensity | 2 |
| Red.Blood.Cell.MeanDensity | 2 |
| Red.Blood.Cell.MinDensity | 0 |
| Red.Blood.Cell.StdDevDensity | 1 |
| Red.Blood.Cell.MaxDiff.ofenclosing. | 0 |
| Red.Blood.Cell.MeanDiff.ofenclosing | 0 |
| Red.Blood.Cell.MinDiff.ofenclosing. | 0 |
| Red.Blood.Cell.StdDevDiff.ofenclosi | 0 |
| Red.Blood.Cell.MaxEllipticFit | 0 |
| Red.Blood.Cell.MeanEllipticFit | 0 |
| Red.Blood.Cell.MinEllipticFit | 1 |
| Red.Blood.Cell.StdDevEllipticFit | 0 |
| Red.Blood.Cell.MaxLengthm | 0 |
| Red.Blood.Cell.MeanLengthm | 0 |
| Red.Blood.Cell.MinLengthm | 3 |
| Red.Blood.Cell.StdDevLengthm | 0 |
| Red.Blood.Cell.SumLengthm | 0 |
| Red.Blood.Cell.MaxMax.Diff. | 0 |
| Red.Blood.Cell.MeanMax.Diff. | 0 |
| Red.Blood.Cell.MinMax.Diff. | 0 |
| Red.Blood.Cell.StdDevMax.Diff. | 0 |
| Red.Blood.Cell.MaxMeanChannel1 | 0 |
| Stroma.MinRadiusofsmallestenclosing | 0 |
| Stroma.StdDevRadiusofsmallestenclos | 0 |
| Stroma.MaxStdevChannel1 | 0 |
| Stroma.MeanStdevChannel1 | 0 |
| Stroma.MinStdevChannel1 | 3 |
| Stroma.StdDevStdevChannel1 | 0 |
| Stroma.MaxStdevChannel2 | 1 |
| Stroma.MeanStdevChannel2 | 0 |
| Stroma.MinStdevChannel2 | 0 |
| Stroma.StdDevStdevChannel2 | 0 |
| Stroma.MaxStdevChannel3 | 0 |
| Stroma.MeanStdevChannel3 | 0 |
| Stroma.MinStdevChannel3 | 1 |
| Stroma.StdDevStdevChannel3 | 0 |
| Stroma.MaxWidthm | 0 |
| Stroma.MeanWidthm | 0 |
| Stroma.MinWidthm | 0 |
| Stroma.StdDevWidthm | 0 |
| Stroma.Nuclei.Objects | 1 |
| Stroma.Nuclei.ObjectsPct | 1 |
| Stroma.Nuclei.MaxAreaPxl | 1 |
| Stroma.Nuclei.MeanAreaPxl | 0 |
| Stroma.Nuclei.MinAreaPxl | 0 |
| Stroma.Nuclei.StdDevAreaPxl | 0 |
| Stroma.Nuclei.SumAreaPxl | 0 |
| Stroma.Nuclei.MaxAsymmetry | 0 |
| Stroma.Nuclei.MeanAsymmetry | 1 |
| Stroma.Nuclei.MinAsymmetry | 0 |
| Stroma.Nuclei.StdDevAsymmetry | 0 |
| Stroma.Nuclei.MaxBorderlengthm | 0 |
| Stroma.Nuclei.MeanBorderlengthm | 0 |
| Stroma.Nuclei.MinBorderlengthm | 0 |
| Stroma.Nuclei.StdDevBorderlengthm | 0 |
| Stroma.Nuclei.SumBorderlengthm | 0 |
| Stroma.Nuclei.MaxBrightness | 1 |
| Stroma.Nuclei.MeanBrightness | 0 |
| Stroma.Nuclei.MinBrightness | 0 |
| Stroma.Nuclei.StdDevBrightness | 1 |
| Stroma.Nuclei.MaxCompactness | 2 |
| Stroma.Nuclei.MeanCompactness | 0 |
| Stroma.Nuclei.MinCompactness | 1 |
| Stroma.Nuclei.StdDevCompactness | 1 |
| Stroma.Nuclei.MaxDensity | 0 |
| Stroma.Nuclei.MeanDensity | 0 |
| Stroma.Nuclei.MinDensity | 1 |
| Stroma.Nuclei.StdDevDensity | 0 |
| Stroma.Nuclei.MaxDiff.ofenclosing.e | 1 |
| Stroma.Nuclei.MeanDiff.ofenclosing. | 0 |

For tissue segmentation, done by the Magic™ system made by Aureon™ Biosciences Corporation of Yonkers, N.Y., image objects are classified as instances of histopathological classes using spectral characteristics, shape characteristics and special relations between tissue histopathological objects. For a given histopathological object, its properties are computed and output as bioimaging features. Properties include both spectral (color channel values, standard deviations and brightness) and generic shape (area, length, width, compactness, density, etc) properties. Statistics (minimum, maximum, mean and standard deviation) are computed for each property specific to a histopathological object. The above is reflected in the names of the features in the Appendix. For example, for the feature "Lumen.StdDevAreaPxl", "Lumen" indicates the histopathological object, "StdDev" indicates the statistic of standard deviation, and "AreaPxl" indicates a property of the object.

Statistics and properties were calculated for the following histopathological objects. "Background" is the portion of the digital image that is not occupied by tissue. "Cytoplasm" is the amorphous "pink" area that surrounds an epithelial nucleus. "Epithelial nuclei" are "round" objects surrounded by cytoplasm. "Lumen" is an enclosed white area surrounded by epithelial cells. Occasionally, the lumen can be filled by prostatic fluid (pink) or other "debris" (e.g., macrophages, dead cells, etc.). Together the lumen and the epithelial nuclei form a gland unit. "Stroma" are a form of connective tissue with different density that maintain the architecture of the prostatic tissue. Stroma are present between the gland units. "Stroma nuclei" are elongated cells with no or minimal amounts of cytoplasm (fibroblasts). This category may also include endothelial cells and inflammatory cells, and epithelial nuclei may also be found scattered within the stroma if cancer is present. "Red blood cells" are small red round objects usually located within the vessels (arteries or veins), but can also be found dispersed throughout tissue AK.1, AK.2, AK.3, AK.4, and AK.5 are user-defined labels with no particular meaning. "C2EN" is a relative ratio of nucleus area to the cytoplasm. The more anaplastic/malignant the epithelial cell is the more area is occupied by the nucleus. "EN2SN" is the percent or relative amount of epithelial to stroma cells present in the digital tissue image. "L2Core" is the number or area of lumen present within the tissue. The higher the Gleason grade the less amount of lumen is present. "C2L" is relative cytoplasm to lumen. "CEN2L" is relative cytoplasm endothelial cells to lumen.

The portions of the names after the objects are exemplary only and correspond to the Cellenger Developer Studio 4.0 software made by Definiens AG of Munich, Germany.

End Appendix.

TABLE 1

Result Summary of Baylor Study

| Model | # of Features | Predictive Accuracy |
|---|---|---|
| Clinical/Histopathological | | |
| No FS | 16 | .79 |
| FS (SVRc-GB) | 13 | .80 |
| IHC | | |
| No FS | 43 | .66 |
| FS (SvRc-GB) | 33 | .76 |
| IMG | | |
| No FS | 496 | .63 |
| FS (SVRc-GB) | 463 | .69 |
| Clinical/Histopathological + IHC + IMG | | |
| No FS (Clinical/Histopathological) | NA | .79 |
| FS (Clinical/Histopathological + SVRC-GF on IHC) | 16 Clinical/Histopathological, 3 IHC | .82 |
| FS (Clinical/Histopathological/IHC + SVRc-GF on IMG) | 16 Clinical/Histopathological, 3 IHC, 2 IMG | .83 |
| FS (SVRc-GB on Clinical/Histopathological/IHC/IMG) | 15 Clinical/Histopathological, 3 IHC, 2 IMG | .83 |

TABLE 2

Experimental Results

| Dataset Investigated | Description | AUC/C Index for Testing sets | | |
|---|---|---|---|---|
| | | Mean | Range Min | Max |
| Clinical/Histopathological Data Only | 130 pts, 16 features | 0.74 | 0.50 | 0.95 |
| IHC-Biomarker Only | 130 pts, 43 features | 0.62 | 0.50 | 0.84 |
| Bio-imaging Data Only | 130 pts, 496 features | 0.62 | 0.51 | 0.84 |
| Clinical/Histopathological + SVRc-GF[IHC-Biomarker]-GB | 130 pts, 59 features | 0.68 | 0.51 | 0.91 |
| (Clinical/Histopathological + SVRc-GF[IHC-Biomarker]-GB)* + SVRc-GF[Bio-imaging]-GB | 130 pts, 555 features | 0.62 | 0.50 | 0.86 |

What is claimed is:

1. A computer-implemented method of producing a model for use in predicting time to occurrence of a health-related condition, the method comprising:
performing with a data regression and analysis device:
obtaining multi-dimensional, non-linear vectors of information indicative of status of multiple test subjects, at least one of the vectors being right-censored, lacking an indication of a time of occurrence of the health-related condition with respect to the corresponding test subject; and
performing regression using the vectors of information to produce a kernel-based model to provide an output value related to a prediction of time to the health-related condition based upon at least some of the information contained in the vectors of information;
wherein for each vector comprising right-censored data, a censored-data penalty function is used to affect the regression, the censored-data penalty function being different than a non-censored-data penalty function used for each vector comprising non-censored data;
wherein performing the regression comprises using penalty functions that include linear functions of a difference between a predicted value of the model and a target value for the predicted value, and wherein a first slope of the linear function for positive differences between the predicted and target values for the censored-data penalty function is lower than a second slope of the linear function for positive differences between the predicted and target values for the non-censored-data penalty function.

2. The method of claim 1 wherein the regression comprises support vector regression.

3. The method of claim 1 wherein the first slope is lower than the magnitude of a slope of the linear function for negative differences between the predicted and target values for the censored-data penalty function.

4. The method of claim 1 wherein the second slope is greater than the magnitude of a slope of the linear function for negative differences between the predicted and target values for the non-censored-data penalty function.

5. The method of claim 1 wherein the first slope is lower than the magnitude of a third slope of the linear function for negative differences between the predicted and target values for the censored-data penalty function and the magnitude of a fourth slope of the linear function for negative differences between the predicted and target values for the non-censored-data penalty function.

6. The method of claim 1 wherein performing the regression comprises using penalty functions that include epsilon values which control how much deviation between predicted and target values is tolerated before a penalty is assessed, wherein a epsilon value for the censored-data penalty function is different than a epsilon value for the non-censored data penalty function.

7. The method of claim 6 wherein a epsilon value of the censored-data penalty function for positive differences between the predicted and target values is greater than at least one of the magnitude of a epsilon value of the censored-data penalty function for negative differences between the predicted and target values, the magnitude of a epsilon value of the non-censored-data penalty function for negative differences between the predicted and target values, and a epsilon value of the non-censored-data penalty function for positive differences between the predicted and target values.

8. The method of claim 6 wherein the magnitude of a epsilon value of the non-censored-data penalty function for negative differences between the predicted and target values is greater than a epsilon value of the non-censored-data penalty function for positive differences between the predicted and target values.

9. The method of claim 1 wherein the model provides an output value indicative of at least one of a time to occurrence of a health-related condition and a probability of occurrence of the health-related condition.

10. The method of claim 1 wherein the vectors include categories of data of clinical/histopathological data, biomarker data, and bio-image data from a computer image of tissue.

11. Apparatus for producing a model for use in predicting time to occurrence of a health-related condition, the apparatus comprising:
a data regression and analysis device configured to:
obtain multi-dimensional, non-linear vectors of information indicative of status of multiple test subjects, at least one of the vectors being right-censored, lacking an indication of a time of occurrence of the health-related condition with respect to the corresponding test subject; and
perform regression using the vectors of information to produce a kernel-based model to provide an output value related to a prediction of time to the health-related condition based upon at least some of the information contained in the vectors of information;
wherein for each vector comprising right-censored data, a censored-data penalty function is used to affect the regression, the censored-data penalty function being different than a non-censored-data penalty function used for each vector comprising non-censored data;
wherein the data regression and analysis device is configured to perform the regression using penalty functions that include linear functions of a difference between a predicted value of the model and a target value for the predicted value, and wherein a first slope of the linear function for positive differences between the predicted and target values for the censored-data penalty function is lower than a second slope of the linear function for positive differences between the predicted and target values for the non-censored-data penalty function.

12. The apparatus of claim 11 wherein the regression comprises support vector regression.

13. The apparatus of claim 11 wherein the first slope is lower than the magnitude of a slope of the linear function for negative differences between the predicted and target values for the censored-data penalty function.

14. The apparatus of claim 11 wherein the second slope is greater than the magnitude of a slope of the linear function for negative differences between the predicted and target values for the non-censored-data penalty function.

15. The apparatus of claim 11 wherein the first slope is lower than the magnitude of a third slope of the linear function for negative differences between the predicted and target values for the censored-data penalty function and the magnitude of a fourth slope of the linear function for negative differences between the predicted and target values for the non-censored-data penalty function.

16. The apparatus of claim 11 wherein the data regression and analysis device configured to perform the regression is configured to use penalty functions that include epsilon values which control how much deviation between predicted and target values is tolerated before a penalty is assessed, wherein a epsilon value for the censored-data penalty function is different than a epsilon value for the non-censored data penalty function.

17. The apparatus of claim 16 wherein a epsilon value of the censored-data penalty function for positive differences between the predicted and target values is greater than at least one of the magnitude of a epsilon value of the censored-data penalty function for negative differences between the predicted and target values, the magnitude of a epsilon value of the non-censored-data penalty function for negative differences between the predicted and target values, and a epsilon value of the non-censored-data penalty function for positive differences between the predicted and target values.

18. The apparatus of claim 16 wherein the magnitude of a epsilon value of the non-censored-data penalty function for negative differences between the predicted and target values is greater than a epsilon value of the non-censored-data penalty function for positive differences between the predicted and target values.

19. The apparatus of claim 11 wherein the model provides an output value indicative of at least one of a time to occurrence of a health-related condition and a probability of occurrence of the health-related condition.

20. The apparatus of claim 11 wherein the vectors include categories of data of clinical/histopathological data, biomarker data, and bio-image data from a computer image of tissue.

21. A computer-implemented method of producing a model for use in predicting time to occurrence of a health-related condition, the method comprising:
performing with a data regression and analysis device:
obtaining multi-dimensional, non-linear vectors of information indicative of status of multiple test subjects; and
performing regression using the vectors of information to produce a kernel-based model to provide an output value related to a prediction of time to the health-related condition based upon at least some of the information contained in the vectors of information;
wherein performing the regression comprises using penalty functions that include linear functions of a difference between a predicted value of the model and a target value for the predicted value, and wherein at least two different penalty functions are used to affect the regression comprising:
a first penalty function used to affect the regression for vectors of information for which a positive difference is present between the predicted and target values; and
a second penalty function, different than the first penalty function, used to affect the regression for vectors of information for which a negative difference is present between the predicted and target values;
wherein the first penalty function is used to affect the regression for at least one of the following types of vectors of information (i) right-censored vectors of information, lacking an indication of a time of occurrence of the health-related condition with respect to the corresponding test subject, for which a positive difference is present between the predicted and target values and (ii) non-censored vectors of information for which a positive difference is present between the predicted and target values; and
the second penalty function is used to affect the regression for at least one of the following types of vectors of information (i) right-censored vectors of information for which a negative difference is present between the predicted and target values and (ii) non-censored vectors of information for which a negative difference is present between the predicted and target values.

22. The method of claim 21 wherein the magnitude of a slope of the linear function for the first penalty function is different than the magnitude of a slope of the linear function for the second penalty function.

23. The method of claim 22 wherein the first penalty function is used for the right-censored vectors of information for which a positive difference is present between the predicted and target values, the second penalty function is used for the right-censored vectors of information for which a negative difference is present between the predicted and target values, and the slope of the linear function for the first penalty function is less than the magnitude of the slope of the linear function for the second penalty function.

24. The method of claim 22 wherein the second penalty function is used for the non-censored vectors of information for which a negative difference is present between the predicted and target values, the first penalty function is used for the non-censored vectors of information for which a positive difference is present between the predicted and target values, and the magnitude of the slope of the linear function for the second penalty function is less than the slope of the linear function for the first penalty function.

25. The method of claim 21 wherein each of the first penalty function and the second penalty function includes an epsilon value which controls how much deviation between the predicted and target values is tolerated before a penalty is assessed, wherein the magnitude of the epsilon value for the first penalty function is different than the magnitude of the epsilon value for the second penalty function.

26. The method of claim 25 wherein the first penalty function is used for the right-censored vectors of information for which a positive difference is present between the predicted and target values, the second penalty function is used for the right-censored vectors of information for which a negative difference is present between the predicted and target values, and the epsilon value for the first penalty function is greater than the magnitude of epsilon value for the second penalty function.

27. The method of claim 25 wherein the second penalty function is used for the non-censored vectors of information for which a negative difference is present between the predicted and target values, the first penalty function is used for the non-censored vectors of information for which a positive difference is present between the predicted and target values, and the magnitude of the epsilon value for the second penalty function is greater than the epsilon value for the first penalty function.

28. A computer program product producing a model for use in predicting time to occurrence of a health-related condition, the computer program product residing on a non-transitory computer readable storage, medium, the computer program product comprising computer- readable, computer-executable instructions for causing a computer to:
obtain multi-dimensional, non-linear vectors of information indicative of status of multiple test subjects; and
perform regression using the vectors of information to produce a kernel-based model to provide an output value related to a prediction of time to the health-related condition based upon at least some of the information contained in the vectors of information;
wherein performing the regression comprises using penalty functions that include linear functions of a difference between a predicted value of the model and a target value for the predicted value, and wherein at least two different penalty functions are used to affect the regression comprising:
a first penalty function used to affect the regression for vectors of information for which a positive difference is present between the predicted and target values; and
a second penalty function, different than the first penalty function, used to affect the regression for vectors of information for which a negative difference is present between the predicted and target values;
wherein the first penalty function is used to affect the regression for at least one of the following types of vectors of information (i) right-censored vectors of information, lacking an indication of a time of occurrence of the health-related condition with respect to the corresponding test subject, for which a positive difference is present between the predicted and target values and (ii) right non-censored vectors of information for which a positive difference is present between the predicted and target values; and
the second penalty function is used to affect the regression for at least one of said the following types of vectors of information (i) right-censored vectors of information for which a negative difference is present between the predicted and target values and (ii) non-censored vectors of information for which a negative difference is present between the predicted and target values.

29. The computer program product of claim 28 wherein the magnitude of a slope of the linear function for the first penalty function is different than the magnitude of a slope of the linear function for the second penalty function.

30. The computer program product of claim 29 wherein the first penalty function is used for the right-censored vectors of information for which a positive difference is present between the predicted and target values, the second penalty function is used for the right-censored vectors of information for which a negative difference is present between the predicted and target values, and the slope of the linear function for the first penalty function is less than the magnitude of the slope of the linear function for the second penalty function.

31. The computer program product of claim 29 wherein the second penalty function is used for the non-censored vectors of information for which a negative difference is present between the predicted and target values, the first penalty function is used for the non-censored vectors of information for which a positive difference is present between the predicted and target values, and the magnitude of the slope of the linear function for the second penalty function is less than the slope of the linear function for the first penalty function.

32. The computer program product of claim 28 wherein each of the first penalty function and the second penalty function includes an epsilon value which controls how much deviation between the predicted and target values is tolerated before a penalty is assessed, wherein the magnitude of the epsilon value for the first penalty function is different than the magnitude of the epsilon value for the second penalty function.

33. The computer program product of claim 32 wherein the first penalty function is used for the right-censored vectors of information for which a positive difference is present between the predicted and target values, the second penalty function is used for the right-censored vectors of information for which a negative difference is present between the predicted and target values, and the epsilon value for the first penalty function is greater than the magnitude of the epsilon value for the second penalty function.

34. The computer program product of claim 32 wherein the second penalty function is used for the non-censored vectors of information for which a negative difference is present between the predicted and target values, the first penalty function is used for the non-censored vectors of information for which a positive difference is present between the predicted and target values, and the magnitude of the epsilon value for the second penalty function is greater than the epsilon value for the first penalty function.

35. Apparatus for producing a model for use in predicting time to occurrence of a health-related condition, the apparatus comprising:
a data regression and analysis device configured to:
obtain multi-dimensional, non-linear vectors of information indicative of status of multiple test subjects; and
perform regression using the vectors of information to produce a kernel-based model to provide an output value related to a prediction of time to the health-related condition based upon at least some of the information contained in the vectors of information;
wherein performing the regression comprises using penalty functions that include linear functions of a difference between a predicted value of the model and a target value for the predicted value, and wherein at least two different penalty functions are used to affect the regression comprising:
a first penalty function used to affect the regression for vectors of information for which a positive difference is present between the predicted and target values; and
a second penalty function, different than the first penalty function, used to affect the regression for vectors of information for which a negative difference is present between the predicted and target values;
wherein the first penalty function is used to affect the regression for at least one of the following types of vectors of information (i) right-censored vectors of information, lacking an indication of a time of occurrence of the health-related condition with respect to the corresponding test subject, for which a positive difference is present between the predicted and target values and (ii) non-censored vectors of information for which a positive difference is present between the predicted and target values; and
the second penalty function is used to affect the regression for at least one of the following types of vectors of information (i) right-censored vectors of information for which a negative difference is present between the predicted and target values and (ii) non-censored vectors of information for which a negative difference is present between the predicted and target values.

36. The apparatus of claim 35 wherein the magnitude of a slope of the linear function for the first penalty function is different than the magnitude of a slope of the linear function for the second penalty function.

37. The apparatus of claim 36 wherein the first penalty function is used for the right-censored vectors of information for which a positive difference is present between the predicted and target values, the second penalty function is used for the right-censored vectors of information for which a negative difference is present between the predicted and target values, and the slope of the linear function for the first penalty function is less than the magnitude of the slope of the linear function for the second penalty function.

38. The apparatus of claim 36 wherein the second penalty function is used for the non-censored vectors of information for which a negative difference is present between the predicted and target values, the first penalty function is used for the non-censored vectors of information for which a positive difference is present between the predicted and target values, and the magnitude of the slope of the linear function for the second penalty function is less than the slope of the linear function for the first penalty function.

39. The apparatus of claim 35 wherein each of the first penalty function and the second penalty function includes an epsilon value which controls how much deviation between the predicted and target values is tolerated before a penalty is assessed, wherein the magnitude of the epsilon value for the first penalty function is different than the magnitude of the epsilon value for the second penalty function.

40. The apparatus of claim 39 wherein the first penalty function is used for the right-censored vectors of information for which a positive difference is present between the predicted and target values, the second penalty function is used for the right-censored vectors of information for which a negative difference is present between the predicted and target values, and the epsilon value for the first penalty function is greater than the magnitude of the epsilon value for the second penalty function.

41. The apparatus of claim 39 wherein the second penalty function is used for the non-censored vectors of information for which a negative difference is present between the predicted and target values, the first penalty function is used for the non-censored vectors of information for which a positive difference is present between the predicted and target values, and the magnitude of the epsilon value for the second penalty function is greater than the epsilon value for the first penalty function.

* * * * *